(12) United States Patent
Joshi et al.

(10) Patent No.: US 8,980,832 B2
(45) Date of Patent: Mar. 17, 2015

(54) USE OF FUMARIC ACID DERIVATIVES FOR TREATING CARDIAC INSUFFICIENCY, AND ASTHMA

(75) Inventors: Rajendra Kumar Joshi, Zürich (CH); Hans-Peter Strebel, Lucerne (CH); Christian Zaugg, Rheinfelden (CH); Michael Tamm, Basel (CH)

(73) Assignee: Biogen Idec International GmbH, Zug (CH)

( * ) Notice: Subject to any disclaimer, the term of this patent is extended or adjusted under 35 U.S.C. 154(b) by 217 days.

(21) Appl. No.: 12/884,573

(22) Filed: Sep. 17, 2010

(65) Prior Publication Data

US 2011/0124615 A1    May 26, 2011

Related U.S. Application Data

(63) Continuation of application No. 10/571,241, filed as application No. PCT/EP2004/009835 on Sep. 3, 2004, now abandoned.

(30) Foreign Application Priority Data

Sep. 9, 2003  (DE) .................................. 103 41 530
Dec. 23, 2003  (DE) .................................. 103 60 869

(51) Int. Cl.
*A61P 9/00*    (2006.01)
*A61K 31/231*    (2006.01)
*A61K 31/573*    (2006.01)

(52) U.S. Cl.
CPC ............. *A61K 31/231* (2013.01); *A61K 31/573* (2013.01)
USPC ....................................................... 514/16.4

(58) Field of Classification Search
CPC ........................... A61K 31/231; A61K 31/573
See application file for complete search history.

(56) References Cited

U.S. PATENT DOCUMENTS

| 4,086,334 A | 4/1978 | Schmidt-Dunker et al. |
| 4,515,974 A | 5/1985 | Zecher et al. |
| 4,746,668 A | 5/1988 | Sato et al. |
| 4,851,439 A | 7/1989 | Speiser et al. |
| 4,959,389 A | 9/1990 | Speiser et al. |
| 5,149,695 A | 9/1992 | Speiser et al. |
| 5,214,196 A | 5/1993 | Blank |
| 5,242,905 A | 9/1993 | Blank |
| 5,248,695 A | 9/1993 | Resemann et al. |
| 5,359,128 A | 10/1994 | Blank |
| 5,424,332 A | 6/1995 | Speiser et al. |
| 5,451,667 A | 9/1995 | Speiser et al. |
| 5,484,610 A | 1/1996 | Bae |
| 5,519,028 A | 5/1996 | Beljanski |
| 5,538,968 A | 7/1996 | Chiesi et al. |
| 5,548,059 A | 8/1996 | Bayley et al. |
| 5,648,386 A | 7/1997 | Resemann et al. |
| 5,650,492 A | 7/1997 | Gately et al. |
| 5,972,363 A | 10/1999 | Clikeman et al. |
| 6,277,882 B1 | 8/2001 | Joshi et al. |
| 6,355,676 B1 | 3/2002 | Joshi et al. |
| 6,359,003 B1 | 3/2002 | Joshi et al. |
| 6,436,992 B1 | 8/2002 | Joshi et al. |
| 6,509,376 B1 | 1/2003 | Joshi et al. |
| 6,537,584 B1 | 3/2003 | Zentner et al. |
| 6,673,516 B2 | 1/2004 | Kumon et al. |
| 6,812,248 B2 | 11/2004 | Zhang et al. |
| 6,830,759 B2 | 12/2004 | Makino et al. |
| 6,858,750 B2 | 2/2005 | Joshi et al. |
| 7,056,950 B2 | 6/2006 | Rath |
| 7,157,423 B2 | 1/2007 | Joshi et al. |

(Continued)

FOREIGN PATENT DOCUMENTS

| CA | 2248955 A1 | 5/1997 |
| CN | 1125141 A | 6/1996 |

(Continued)

OTHER PUBLICATIONS

Joseph Pye et al., Proteasone inhibition ablates activation of NF-kB in myocardial reperfusion and reduces reperfusion injury, Am J Physiol Heart Circ Physiol, vol. 284, Nov. 7, 2002, pp. 919-926.*
Bacharach-Buhles, M., et al., "Fumaric Acid Esters (FAEs) Suppress CD 15- and ODP 4-positive Cells in Psoriasis," *Acta. Derm. Venereol.* (*Stockh*) Suppl. 186:79-82, Scandinavian University Press, Sweden (1994).

(Continued)

*Primary Examiner* — Lezah Roberts
*Assistant Examiner* — Nannette Holloman
(74) *Attorney, Agent, or Firm* — Jones Day

(57) ABSTRACT

According to a first aspect the invention relates to the use of fumaric acid derivatives selected from the group consisting of dialkyl fumarates, monoalkyl hydrogen fumarates, fumaric acid monoalkyl ester salts, fumaric acid monoamides, monoamido fumaric acid salts, fumaric acid diamides, monoalkyl monoamido fumarates, carbocyclic and oxacarbocyclic oligomers of these compounds and mixtures thereof for preparing a drug for the treatment or prevention of cardiac insufficiency, in particular left ventricular insufficiency, myocardial infarction and angina pectoris.

According to a second aspect the invention relates to the use of fumaric acid derivatives, selected from the group consisting of dialkyl fumarates, monoalkyl hydrogen fumarates, fumaric acid monoalkyl ester salts, fumaric acid monoamides, monoamido fumaric acid salts, fumaric acid diamides, monoalkyl monoamido fumarates, carbocyclic and oxacarbocyclic oligomers of these compounds and mixtures thereof for preparing a drug for the treatment of asthma and chronic obstructive pulmonary diseases, especially asthma caused by allergies, infections, analgesics, job conditions or physical effort, mixed forms of asthma, or asthma cardiale.

13 Claims, 4 Drawing Sheets

(56) References Cited

U.S. PATENT DOCUMENTS

| | | |
|---|---|---|
| 7,279,331 B2 | 10/2007 | Black et al. |
| 7,320,999 B2 | 1/2008 | Joshi et al. |
| 7,364,900 B2 | 4/2008 | Black et al. |
| 7,417,045 B2 | 8/2008 | Anilkumar et al. |
| 7,432,240 B2 | 10/2008 | Joshi et al. |
| 7,612,110 B2 | 11/2009 | Joshi et al. |
| 7,619,001 B2 | 11/2009 | Joshi et al. |
| 7,638,119 B2 | 12/2009 | Johnson et al. |
| 7,709,025 B2 | 5/2010 | Fegely et al. |
| 7,790,916 B2 | 9/2010 | Joshi et al. |
| 7,803,840 B2 | 9/2010 | Joshi et al. |
| 7,871,977 B2 | 1/2011 | Rischer et al. |
| 7,906,659 B2 | 3/2011 | Joshi et al. |
| 7,915,310 B2 | 3/2011 | Joshi et al. |
| 8,067,467 B2 | 11/2011 | Joshi et al. |
| 8,148,414 B2 | 4/2012 | Gangakhedkar et al. |
| 8,399,514 B2 | 3/2013 | Lukashev et al. |
| 8,524,773 B2 | 9/2013 | Joshi et al. |
| 2003/0176365 A1 | 9/2003 | Blass |
| 2003/0229003 A1 | 12/2003 | Oettgen et al. |
| 2004/0054001 A1* | 3/2004 | Joshi et al. ............... 514/527 |
| 2005/0245612 A1 | 11/2005 | Blass |
| 2007/0027076 A1 | 2/2007 | Joshi et al. |
| 2008/0089861 A1 | 4/2008 | Went et al. |
| 2008/0227847 A1 | 9/2008 | Nilsson et al. |
| 2008/0233185 A1 | 9/2008 | Joshi et al. |
| 2008/0274182 A1 | 11/2008 | Alida Boekema et al. |
| 2008/0300217 A1 | 12/2008 | Nilsson |
| 2009/0304790 A1 | 12/2009 | Nilsson et al. |
| 2010/0093611 A1 | 4/2010 | Horrigan et al. |
| 2010/0130607 A1 | 5/2010 | Gold |
| 2011/0112196 A1 | 5/2011 | Lukashev |
| 2011/0124615 A1 | 5/2011 | Joshi et al. |
| 2011/0293711 A1 | 12/2011 | Joshi et al. |
| 2012/0165404 A1 | 6/2012 | Lukashev |
| 2012/0196931 A1 | 8/2012 | Lukashev et al. |
| 2012/0259012 A1 | 10/2012 | Lukashev |
| 2013/0216615 A1 | 8/2013 | Goldman |
| 2013/0287732 A1 | 10/2013 | Goelz et al. |
| 2013/0295169 A1 | 11/2013 | Goldman et al. |
| 2013/0302410 A1 | 11/2013 | Gold |
| 2013/0303613 A1 | 11/2013 | Lukashev |
| 2013/0315993 A1 | 11/2013 | Nilsson et al. |
| 2013/0316003 A1 | 11/2013 | Nilsson et al. |
| 2013/0317103 A1 | 11/2013 | Lukashev |
| 2014/0037720 A1 | 2/2014 | Nilsson et al. |
| 2014/0037740 A1 | 2/2014 | Nilsson et al. |
| 2014/0066505 A1 | 3/2014 | Joshi et al. |
| 2014/0099364 A2 | 4/2014 | Nilsson et al. |

FOREIGN PATENT DOCUMENTS

| | | |
|---|---|---|
| DE | 25 30 372 A1 | 1/1977 |
| DE | 26 21 214 A1 | 11/1977 |
| DE | 28 40 498 B1 | 8/1979 |
| DE | 38 34 794 A1 | 4/1990 |
| DE | 40 14 252 A1 | 11/1991 |
| DE | 197 21 099 A1 | 11/1998 |
| DE | 198 39 566 A1 | 3/2000 |
| DE | 198 53 487 A1 | 5/2000 |
| DE | 100 00 577 A1 | 7/2001 |
| DE | 101 33 004.9 | 7/2001 |
| DE | 101 01 307 A1 | 8/2002 |
| DE | 102 17 314 A1 | 11/2003 |
| EP | 0 103 274 A2 | 3/1984 |
| EP | 0 188 749 A2 | 7/1986 |
| EP | 0 312 697 A2 | 4/1989 |
| EP | 0 518 388 A2 | 12/1992 |
| EP | 0 312 697 B1 | 4/1993 |
| EP | 0 354 921 B1 | 10/1996 |
| EP | 0 793 966 A1 | 9/1997 |
| EP | 0 852 233 A1 | 7/1998 |
| EP | 0 605 700 B1 | 5/2000 |
| EP | 1 051 159 B1 | 4/2002 |
| EP | 0 699 070 B1 | 9/2002 |
| EP | 1 663 197 B1 | 6/2006 |
| EP | 1 913 942 B1 | 4/2008 |
| EP | 2 056 834 B1 | 8/2012 |
| EP | 1 485 078 B1 | 9/2012 |
| EP | 2 379 063 B1 | 3/2013 |
| GB | 1 153 927 A | 6/1969 |
| GB | 2 176 999 A | 1/1987 |
| GB | 2 291 422 A | 1/1996 |
| JP | 52-083957 | 7/1977 |
| JP | 54-80439 A | 6/1979 |
| JP | 6-345644 A | 12/1994 |
| JP | 8-99906 A | 4/1996 |
| JP | 9-221428 A | 8/1997 |
| RU | 2002737 C1 | 11/1993 |
| RU | 2 189 813 C1 | 9/2002 |
| WO | WO 89/01930 A1 | 3/1989 |
| WO | WO 94/28883 A1 | 12/1994 |
| WO | WO 95/12572 A1 | 5/1995 |
| WO | WO 95/25102 A1 | 9/1995 |
| WO | WO 96/01122 A1 | 1/1996 |
| WO | WO 96/08970 A1 | 3/1996 |
| WO | WO 9627369 A2 * | 9/1996 ............. A61K 31/19 |
| WO | WO 97/09984 A1 | 3/1997 |
| WO | WO 97/13504 A1 | 4/1997 |
| WO | WO 97/44054 A2 | 11/1997 |
| WO | WO 97/48405 A1 | 12/1997 |
| WO | WO 98/04290 A2 | 2/1998 |
| WO | WO 98/27970 A2 | 7/1998 |
| WO | WO 98/52549 A2 | 11/1998 |
| WO | WO 99/21565 A1 | 5/1999 |
| WO | WO 00/30622 A2 | 6/2000 |
| WO | WO 01/59072 A1 | 8/2001 |
| WO | WO 02/02190 A2 | 1/2002 |
| WO | WO 02/38142 A2 | 5/2002 |
| WO | WO 02/055063 A2 | 7/2002 |
| WO | WO 02/055067 A2 | 7/2002 |
| WO | WO 02055067 A2 * | 7/2002 ........... A61K 31/194 |
| WO | WO 02/064129 A2 | 8/2002 |
| WO | WO 03/004001 A1 | 1/2003 |
| WO | WO 03/020908 A2 | 3/2003 |
| WO | WO 03/032969 A2 | 4/2003 |
| WO | WO 03/080034 A2 | 10/2003 |
| WO | WO 03/087174 A2 | 10/2003 |
| WO | WO 03/088958 A2 | 10/2003 |
| WO | WO 2005/016318 A1 | 2/2005 |
| WO | WO 2005/023241 A1 | 3/2005 |
| WO | WO 2005/027899 A1 | 3/2005 |
| WO | WO 2006/037342 A2 | 4/2006 |
| WO | WO 2006/050730 A1 | 5/2006 |
| WO | WO 2006/055871 A2 | 5/2006 |
| WO | WO 2006/088836 A2 | 8/2006 |
| WO | WO 2006/088837 A2 | 8/2006 |
| WO | WO 2006/088840 A1 | 8/2006 |
| WO | WO 2006/088919 A2 | 8/2006 |
| WO | WO 2006/088920 A1 | 8/2006 |
| WO | WO 2006/088921 A2 | 8/2006 |
| WO | WO 2006/091428 A2 | 8/2006 |
| WO | WO 2007/005879 A2 | 1/2007 |
| WO | WO 2007/006307 A2 | 1/2007 |
| WO | WO 2007/006308 A1 | 1/2007 |
| WO | WO 2007/042034 A1 | 4/2007 |
| WO | WO 2007/042035 A2 | 4/2007 |
| WO | WO 2008/096271 A2 | 8/2008 |
| WO | WO 2008/097596 A2 | 8/2008 |
| WO | WO 2010/079222 A1 | 7/2010 |
| WO | WO 2010/126605 A1 | 11/2010 |
| WO | WO 2011/100589 A1 | 8/2011 |
| WO | WO 2012/162669 A1 | 11/2012 |
| WO | WO 2012/170923 A1 | 12/2012 |
| WO | WO 2013/090799 A1 | 6/2013 |
| WO | WO 2013/119677 A1 | 8/2013 |
| WO | WO 2013/171345 A1 | 11/2013 |

OTHER PUBLICATIONS

Itoh, H., *Japan J. Interv. Cardiol.* 18 (Suppl. 1):93 (2003).
Kurabayashi, M., *Shindan to Chiryo* 88:2079-2086 (2000).
Matsumori, A., *Igaku no Ayumi* 206:793-798 (2003).

(56) References Cited

OTHER PUBLICATIONS

McDonald, C.J. and Calabresi, P., "Psoriasis and Occlusive Vascular Disease," *Br. J. Dermatol.* 99:469-475, British Association of Dermatologists, England (1978).
Pye, J., et al., "Proteasome Inhibition Ablates Activation of NF-κB in Myocardial Reperfusion and Reduces Reperfusion Injury," *Am. J. Physiol. Heart Circ. Physiol.* 284:H919-H926, American Physiological Society, United States (2002).
Material Safety Data Sheet for Dimethyl fumarate, SIGMA-ALDRICH, accessed at: http://www.sigmaaldrich.com/MSDS: accessed on Jun. 20, 2012, 6 pages.
Shimizu, M., *Jpn. J. Thorac. Cardiovasc. Surg.* 50 (Suppl.):212 (2002).
Gutzmer, R., et al. "Successful Treatment of Cutaneous and Pulmonary Sarcoidosis Using Fumaric Acid Esters," *Dermatologist* 55:553-557 (2004).
Pernis, A.B. and Rothman, P.B., "JAK-STAT Signaling in Asthma," *J. Clin. Invest.* 109:1279-1283, American Society for Clinical Investigation, United States (2002).
Luft, R., "The Development of Mitochondrial Medicine," *Proc. Natl. Acad. Sci. USA* 91:8731-8738, National Academy of Sciences, United States (1994).
Musiek, E.S., et al., "Cyclopentenone Isoprostanes Are Novel Bioactive Products of Lipid Oxidization Which Enhance Neurodegeneration," *J. Neurochem.* 97:1301-1313, International Society for Neurochemistry, England (2006).
Göser, S., et al., "Critical Role for Monocyte Chemoattractant Protein-1 and Macrophange Inflammatory Protein-1α in Induction of Experimental Autoimmune Myocarditis and Effective Anti-Monocyte Chemoattractant Protein-1 Gene Therapy," *Circulation* 112:3400-3407, American Heart Association, Inc., United States (2005).
Kawamura, N., et al., "Blockade of NF-κB Improves Cardiac Function and Survival without Affecting Inflammation TNF-1α-induced Cardiomyopathy," *Cardiovasc. Res.* 66:520-529, Elsevier B.V., Netherlands (2005).
Frangogiannis, N.G. and Entman, M.L., "Chemokines in Myocardial Ischemia," *Trends Cardiovasc. Med.* 15(5):163-169, Elsevier Inc., United States (2005).
Azzawi, M., et al., "The Distribution of Cardiac Macrophages in Myocardial Ischaemia and Cardiomyopathy," *Histopathology* 46:314-319, Blackwell Publishing Limited, England (2005).
McGeer, P.L. and McGeer, E.G., "Inflammation and Neurodegeneration in Parkinson's Disease," *Parkinsonism Relat. Disord.* 10:S3-S7, Elsevier Ltd., England (2004).
Nordberg, A., "Pharmacological Treatment of Cognitive Dysfunction in Dementia Disorders," *Acta Neurol. Scand. Suppl.* 168:98-92, Acta Neurologica Scandinavia, Denmark (1996).
Wallace, D.C., "Mitochondrial Diseases in Man and Mouse," *Science* 283:1482-1488, American Association for the Advancement of Science, United States (1999).
Kalenich, O., "Mycardial Remodeling—a Basic Link in the Development of Circulatory Failure during Myocarditis," *Russian J. Cardiology* 3:1-6, International Academy of Cardiology, Russia (1999) (certified translation).
Office Action mailed Feb. 12, 2007, in U.S. Appl. No. 10/250,983, Joshi et al., § 371(c) date Jul. 10, 2003 (now abandoned).
Office Action mailed Jul. 20, 2006, in U.S. Appl. No. 10/250,983, Joshi et al., § 371(c) date Jul. 10, 2003 (now abandoned).
Office Action mailed Nov. 14, 2008, in U.S. Appl. No. 11/833,150, Joshi et al., filed Aug. 2, 2007 (now abandoned).
Office Action mailed on Jul. 13, 2011, in U.S. Appl. No. 12/526,296, Lukashev et al., filed Jan. 13, 2011.
Office Action mailed Mar. 20, 2012, in U.S. Appl. No. 12/525,805, Gold, § 371(c) date Feb. 1, 2010.
Office Action mailed on Dec. 15, 2012, in U.S. Appl. No. 11/914,426, Joshi et al., filed May 23, 2008 (now U.S. Patent No. 8,067,467 B2).

Wang, L. and Lin, S., "Induction of Quinone Reductase and Glutathione-s-transferase by Dimethyl Fumarate in Rats," *Zhonghua Yu Fang Yi Xue Za Zhi* 33(6):366-368, Zhonghua Yi Xue Hui, China (1999).
Wang, L. and Lin, S., "Induction of Quinone Reductase and Glutathione-s-transferase by Dimethyl Fumarate in Rats," *Zhonghua Yu Fang Yi Xue Za Zhi* 33(6):366-368, Zhonghua Yi Xue Hui, China (1999) (English Abstract).
Japanese Office Action dated Jun. 26, 2009 for Japanese Patent Application No. 2006-515290.
Stacey, M. et al., "The Allergen Der p1 Induced NF-κB Activation through Interference with IκBα Function in Asthmatic Bronchial Epithelial Cells," *Biochemical and Biophysical Research Communications* 236:522-526, Academic Press, United States (1997).
Barnes, P. and Adcock, I., "NF-κB: a pivotal role in asthma and a new target for therapy," *Trends in Pharmacological Science* 18(2):46-50, Elsevier Science Ltd., England (1997).
Mue, S., "Signal Transduction and Transcription; Asthma and Signal Transduction and Transcription," *Asthma* 3(4):15-24 (2000).
Fujimara, M., "*Drug Treatment*," The Journal of the Japanese Respiratory Society 39:44, (2001).
Papi, A. et al., "Rhinovirus Infection Induces Expression of Its Own Receptor Intercellular Adhesion Molecule 1 (ICAM-1) via Increased NF-κB-meditated Transcription," *J. Biol. Chem.* 274(14):9707-9720, American Society for Biochemistry and Molecular Biology, Inc., United States (1999).
Yamaya, M., "Studies on the Pathogenesis and Treatment of Virus Infection-Induced Pulmonary Disease," *Respiration* 17(10):1124-1130 (1998).
Japanese Office Action dated Jul. 17, 2012 for Japanese Patent Application No. 2009-292569.
Office Action mailed Apr. 26, 2000, in U.S. Appl. No. 09/194,862, Joshi et al., § 371(c) date Apr. 1, 1998 (now U.S. Patent No. 6,436,992 B1).
Office Action mailed Oct. 31, 2000, in U.S. Appl. No. 09/402,103, Joshi et al., § 371(c) date Dec. 8, 1998 (now U.S. Patent No. 6,277,882 B1).
Office Action mailed Mar. 23, 2004, in U.S. Appl. No. 10/148,858, Joshi et al., § 371(c) date May 28, 2002 (now U.S. Patent No. 6,858,750 B2).
Office Action mailed Aug. 12, 2003, in U.S. Appl. No. 10/148,858, Joshi et al., § 371(c) date May 28, 2002 (now U.S. Patent No. 6,858,750 B2).
Office Action mailed Jan. 10, 2006, in U.S. Appl. No. 10/433,295, Joshi et al., § 371(c) date Jun. 2, 2003 (now U.S. Patent No. 7,157,423 B2).
Office Action mailed Apr. 22, 2005, in U.S. Appl. No. 10/433,295, Joshi et al., § 371(c) date Jun. 2, 2003 (now Patent No. 7,157,423 B2).
Office Action mailed Sep. 9, 2004, in U.S. Appl. No. 10/433,295, Joshi et al., § 371(c) date Jun. 2, 2003 (now U.S. Patent No. 7,157,423 B2).
Office Action mailed Dec. 14, 2007, in U.S. Appl. No. 11/421;083, Joshi et al., filed May 31, 2006 (now U.S. Patent No. 7,432,240 B2).
Office Action mailed May 8, 2007, in U.S. Appl. No. 11/421,083, Joshi et al., filed May 31, 2006 (now U.S. Patent No. 7,432,240 B2).
Office Action mailed Mar. 4, 2002, in U.S. Appl. No. 09/831,620, Joshi et al., § 371(c) date May 10, 2001 (now U.S. Patent 6,509,376 B1).
Office Action mailed May 15, 2007, in U.S. Appl. No. 10/197,077, Joshi et al., filed Jul. 17, 2002 (now U.S. Patent No. 7,320,999 B2).
Office Action mailed Mar. 22, 2004, in U.S. Appl. No. 10/197,077, Joshi et al., filed Jul. 17, 2002 (now U.S. Patent No. 7,320,999 B2).
Office Action mailed Mar. 12, 2009, in U.S. Appl. No. 11/765,563, Joshi et al., filed Jun. 20, 2007 (now U.S. Patent No. 7,612,110 B2).
Office Action mailed Sep. 9, 2008, in U.S. Appl. No. 11/765,563, Joshi et al., filed Jun. 20, 2007 (now U.S. Patent No. 7,612,110 B2).
Office Action mailed Dec. 3, 2007, in U.S. Appl. No. 11/765,563, Joshi et al., filed Jun. 20, 2007 (now U.S. Patent No. 7,612,110 B2).
Office Action mailed Mar. 30, 2009, in U.S. Appl. No. 11/765,578, Joshi et al., filed Jun. 20, 2007 (now U.S. Patent No. 7,619,001 B2).
Office Action mailed Sep. 15, 2008, in U.S. Appl. No. 11/765,578, Joshi et al., filed Jun. 20, 2007 (now U.S. Patent No. 7,619,001 B2).

(56) References Cited

OTHER PUBLICATIONS

Office Action mailed Jul. 25, 2008, in U.S. Appl. No. 11/765,578, Joshi et al., filed Jun. 20, 2007 (now U.S. Patent No. 7,619,001 B2).
Office Action mailed Dec. 14, 2007, in U.S. Appl. No. 11/765,578, Joshi et al., filed Jun. 20, 2007 (now U.S. Patent No. 7,619,001 B2).
Office Action mailed May 20, 2010, in U.S. Appl. No. 12/405,661, Joshi et al., filed Mar. 17, 2009 (now U.S. Patent No. 7,803,840 B2).
Office Action mailed Jan. 19, 2010, in U.S. Appl. No. 12/405,661, Joshi et al., filed Mar. 17, 2009 (now U.S. Patent No. 7,803,840 B2).
Office Action mailed Oct. 2, 2009, in U.S. Appl. No. 12/405,661, Joshi et al., filed Mar. 17, 2009 (now U.S. Patent No. 7,803,840 B2).
Office Action mailed Sep. 9, 2010, in U.S. Appl. No. 12/405,665, Joshi et al., filed Mar. 17, 2009 (now U.S. Patent No. 7,915,310 B2).
Office Action mailed Mar. 23, 2010, in U.S. Appl. No. 12/405,665, Joshi et al., filed Mar. 17, 2009 (now U.S. Patent No. 7,915,310 B2).
Office Action mailed May 21, 2001, in U.S. Appl. No. 09/743,978, Joshi et al., § 371(c) date Oct. 8, 1999 (now U.S. Patent No. 6,355,676 B1).
Office Action mailed Nov. 25, 2009, in U.S. Appl. No. 10/511,564, Joshi et al., § 371(c) date Oct. 15, 2004 (now U.S. Patent No. 7,790,916 B2).
Office Action mailed Apr. 3, 2009, in U.S. Appl. No. 10/511,564, Joshi et al., § 371(c) date Oct. 15, 2004 (now U.S. Patent No. 7,790,916 B2).
Office Action mailed Aug. 11, 2008, in U.S. Appl. No. 10/511,564, Joshi et al., § 371(c) date Oct. 15, 2004 (now U.S. Patent No. 7,790,916 B2).
Office Action mailed Apr. 10, 2008, in U.S. Appl. No. 10/511,564, Joshi et al., § 371(c) date Oct. 15, 2004 (now U.S. Patent No. 7,790,916 B2).
Office Action mailed Oct. 1, 2007, in U.S. Appl. No. 10/511,564, Joshi et al., § 371(c) date Oct. 15, 2004 (now U.S. Patent No. 7,790,916 B2).
Office Action mailed Apr. 9, 2007, in U.S. Appl. No. 10/511,564, Joshi et al., § 371(c) date Oct. 15, 2004 (now U.S. Patent No. 7,790,916 B2).
Office Action mailed Dec. 15, 2011, in U.S. Appl. No. 12/526,296, Lukashev et al., § 371(c) date Jan. 13, 2011 (now abandoned).
Office Action mailed Jul. 13, 2011, in U.S. Appl. No. 12/526,296, Lukashev et al., § 371(c) date Jan. 13, 2011 (now abandoned).
Office Action mailed Oct. 12, 2012, in U.S. Appl. No. 13/372,426, Lukashev, filed Feb. 13, 2012.
Office Action mailed May 3, 2012, in U.S. Appl. No. 13/372,426, Lukashev, filed Feb. 13, 2012.
Office Action mailed Aug. 28, 2012, in U.S. Appl. No. 13/465,740, Lukashev, filed May 7, 2012.
Office Action mailed Mar. 18, 2010, in U.S. Appl. No. 10/571,241, Joshi et al., § 371(c) date Mar. 9, 2006 (now abandoned).
Office Action mailed Sep. 21, 2009, in U.S. Appl. No. 10/571,241, Joshi et al., § 371(c) date Mar. 9, 2006 (now abandoned).
Office Action mailed Mar. 18, 2009, in U.S. Appl. No. 10/571,241, Joshi et al., § 371(c) date Mar. 9, 2006 (now abandoned).
Office Action mailed Sep. 4, 2008, in U.S. Appl. No. 10/571,241, Joshi et al., § 371(c) date Mar. 9, 2006 (now abandoned).
Co-pending Application, U.S. Appl. No. 13/612,221, inventor Joshi et al., filed Sep. 26, 2012 (Not Published).
Inagaki, N., *Allergy Department* 11(1):1-8, Japan (2001).
Sagara, H., *Therapeutics* 32(1):53-56, Japan (1998).
Takayam, T., et al., *Pediatric Department* 43(10): 1454-1460, Japan (2002).
Japanese Office Action mailed Mar. 15, 2013 in Japanese Patent Application No. 2009-292569, Japanese Patent Office.
U.S. Appl. No. 14/209,480, filed Mar. 13, 2014 (Not Published).
U.S. Appl. No. 14/209,584, filed Mar. 13, 2014 (Not Published).
U.S. Appl. No. 14/209,651, filed Mar. 13, 2014 (Not Published).
U.S. Appl. No. 14/209,712, filed Mar. 13, 2014 (Not Published).
U.S. Appl. No. 14/209,756, filed Mar. 13, 2014 (Not Published).
U.S. Appl. No. 14/209,823, filed Mar. 13, 2014 (Not Published).
U.S. Appl. No. 14/212,503, filed Mar. 14, 2014 (Not Published).
U.S. Appl. No. 14/212,685, filed Mar. 14, 2014 (Not Published).
U.S. Appl. No. 14/213,321, filed Mar. 14, 2014 (Not Published).
U.S. Appl. No. 14/213,399, filed Mar. 14, 2014 (Not Published).
U.S. Appl. No. 14/213,673, filed Mar. 14, 2014 (Not Published).
U.S. Appl. No. 14/264,653, inventor Ralf Gold, filed Apr. 29, 2014 (Not Published).
U.S. Appl. No. 14/119,373, inventors Dawson, K., et al., filed Feb. 18, 2014 (Not Published).
U.S. Appl. No. 14/124,562, inventors Guzowski, J., et al., § 371 (c) date: Mar. 11, 2014 (Not Published).
U.S. Appl. No. 14/201,380, inventor Jianhua Chao, filed Mar. 7, 2014 (Not Published).
Allowed Claims for U.S. Appl. No. 13/957,117, filed Aug. 1, 2013.
Allowed Claims for U.S. Appl. No. 13/957,220, filed Aug. 1, 2013.
Thomson Innovation Patent Record, DWPI Accession No. 1979-58797B, English language Abstract of Japanese Patent Publication No. 54-80439 A, (1979).
English language Abrstract of German Patent Publication No. DE 38 34 794 A1, European Patent Office, Espacenet database—Worldwide (2001).
English language Abstract of Japanese Patent Publication No. JP 6-345644 A, European Patent Office, Espacenet database—Worldwide (2001).
English language Abstract of Japanese Patent Publication No. JP 8-99906 A, European Patent Office, Espacenet database—Worldwide (2001).
English language Abstract of Japanese Patent Publication No. JP 9-221428 A, European Patent Office, Espacenet database—Worldwide (2001).
English language Abstract of WIPO Patent Publication No. WO 97/48405 A1, European Patent Office, Espacenet database—Worldwide (2001).
English language Abstract of Russian Patent Publication No. RU 2 189 813 C1, European Patent Office, Espacenet database—Worldwide (2002).
English language Abstract of WIPO Patent Publication No. WO 2005/027899 A1, European Patent Office, Espacenet database—Worldwide (2005).
Altmeyer, P.J., et al., "Antisoriatic effect of fumaric acid derivatives Results of a multicenter double-blind study in 100 patients," *Journal of the American Academy of Dermatology* 30(6):977-981, American Academy of Dermatology, Inc., United States (1994).
Andersson, M. et al., "Cytokine profile in interferon-β treated multiple sclerosis patients: reduction of interleukin-10 mRNA expressing cells in peripheral blood," *Eur. J. Neurol.* 4:567-571, Rapid Science Publishers, England (1997).
Balashov, K.E., et al., "Defective regulation of IFNγ and IL-12 by endogenous IL-10 in progressive MS," *Neurology* 55:192-198, AAN Enterprises, Inc., United States (2000).
Becanovic, K., et al., "Paradoxical effects of arthritis-regulating chromosome 4 regions on myelin oligodendrocyte glycoprotein-induced encephalomyelitis in congenic rats," *Eur. J. Immunol.* 33:1907-1916, Wiley-VCH Verlag GmbH & Co. KGaA, Germany (2003).
Bettelli, E. and Nicholson, L.B., "The Role of Cytokines in Experimental Autoimmune Encephalomyelitis," *Arch. Immun. Ther. Exp.* 48:389-398, Warszawa, Panstwowy Zaklad Wydawn Lekarskich, Switzerland (2000).
Brown, T.R. and Kraft, G.H., "Multiple Sclerosis: A Paradigm Shift," *Phys. Med. Rehabil. Clin. N. Am.* 16:xvii-xx, Elsevier Inc., United States (2005).
Cannella, B., et al., "IL-10 Fails to Abrogate Experimental Autoimmune Encephalomyelitis," *J. Neuroscience Research* 45:735-746, Wiley-Liss, Inc., United States (1996).
Correale, J., et al., "Sulfasalazine aggravates experimental autoimmune encephalomyelitis and causes an increase in the number of autoreactive T cells," *J. Neuroimmunol.* 34:109-120, Elsevier Science Publishers B.V., Netherlands (1991).
Dahlman, I., et al., "Quantitative trait loci disposing for both experimental arthritis and encephalomyelitis in the DA rat; impact on severity of myelin oligodendrocyte glycoprotein-induced experimental autoimmune encephalomyelitis and antibody isotype pattern," *Eur. J. Immunol.* 28:2188-2196, Wiley-VCH Verlag GmbH, Germany (1998).

(56) References Cited

OTHER PUBLICATIONS

Dal Canto, R.A., et al., "Local Delivery of TNF by Retrovirus-Transduced T Lymphocytes Exacerbates Experimental Autoimmune Encephalomyelitis," *Clinical Immunol.* 90(1):10-14, Academic Press, United States (1999).

De Graaf, K.L., et al., "MHC Class II Isotype- and Allele-Specific Attenuation of Experimental Autoimmune Encephalomyelitis," *J. Immunol.* 173:2792-2802, The American Association of Immunologists, Inc., United States (2004).

De Haan, P., "The Risk of Sensibilization and Contact Urticaria upon Topical Application of Fumaric Acid Derivatives," *Dermatology* 188:126-130, Karger AG, Switzerland (1994).

De Jong, R., et al., "Selective stimulation of T helper 2 cytokine responses by the anti-psoriasis agent monomethylfumarate," *Eur. J. Immunol.* 26:2067-2074, Verlag Chemie GmbH, Germany (1996).

Del Prete, G., "The Concept of Type-1 and Type-2 Helper T Cells and Their Cytokines in Humans," *Intern. Rev. Immunol.* 16:427-455, OPA (Overseas Publishers Association) Amsterdam B.V., England (1998).

Dethlefsen, L.A., "Toxic Effects of Acute Glutathione Depletion by Buthionine Sulfoximine and Dimethylfumarate on Murine Mammary Carcinoma Cells," *Radiation Res.* 114:215-224, Academic Press, Inc., United States (1988).

Di Marco, R., et al., "Curative effects of recombinant human Interleukin-6 in DA rats with protracted relapsing experimental allergic encephalomyelitis," *J. Neuroimmunol.* 116:168-177, Elsevier Science B.V., Netherlands (2001).

Di Rosa, F., et al., "Lack of Th2 cytokine increase during spontaneous remission of experimental allergic encephalomyelitis," *Eur. J. Immunol.* 28:3893-3903, Wiley-VCH Verlag GmbH, Germany (1998).

Djerbi, M., et al., "Expression of the Long Form of Human FLIP by Retroviral Gene Transfer of Hemopoietic Stem Cells Exacerbates Experimental Autoimmune Encephalomyelitis," *J. Immunol.* 170:2064-2073, The American Association of Immunologists, Inc., United States (2003).

Dücker, P. and Pfeiff, B., "Zwei Fälle von Nebenwirkungen einer Fumarsäureester-Lokaltharapie," *H+G Zeitschrift für Hautkrankheiten* 65:734-736, Grosse Verlag Berlin, Germany (1990) (Abstract Only in English).

Ferber, I.A., et al., "Mice with a Disrupted IFN-γ Gene Are Susceptible to the Induction of Experimental Autoimmune Encephalomyelitis (EAE)," *J. Immunol.* 156:5-7, The American Association of Immunologists, United States (1996).

Ferrante, P., et al., "Cytokine Production and Surface Marker Expression in Acute and Stable Multiple Sclerosis: Altered IL-12 Production and Augmented Signaling Lymphocytic Activation Molecule (SLAM)—Expressing Lymphocytes in Acute Multiple Sclerosis," *J. Immunol.* 160:1514-1521, The American Association of Immunologists, United States 1998.

Fliegner, L. and Spiegel, P., "Osteomalazie als offenbar seltene Nebenwirkung der oralen Fumarsäuretherapie," *Hautarzt* 43:554-560, Springer-Verlag, Germany (1992) (Abstract Only in English).

Furlan, R., et al., "Interferon-β treatment in multiple sclerosis patients decreases the number of circulating T cells producing interferon-γ and interleukin-4," *J. Neuroimmunol.* 111:86-92, Elsevier Science B.V., Netherlands (2000).

Galli, G., et al., "Macrophage-derived chemokine production by activated human T cells in vitro and in vivo: preferential association with the production of type 2 cytokines," *Eur. J. Immunol.* 30:204-210, Wiley-VCH Verlag GmbH, Germany.

Gasser, M., et al., "Host Vs Graft and Graft Vs Host Reactions After Allogeneic Heterotopic Small Bowel Transplantation in the Rat," *Transplant. Proc.* 24(3):1128-1129, Appleton & Lange, United States (1992).

Genain, C.P., et al., "Late Complications of Immune Deviation Therapy in a Nonhuman Primate," *Science* 274:2054-2057, American Association for the Advancement of Science, United States (1996).

Ghoreschi, K. and Röcken, M., "Immune Deviation Strategies in the Therapy of Psoriasis," *Current Drug Targets—Inflammation & Allergy* 3:193-198, Bentham Science Publishers Ltd., Netherlands (2004).

Ghoreschi, K., et al., "Fumarates induce a DC2 phenotype in dendritic cells that establishes protective Th2 responses," *Arch. Dermatol. Forschung* 296:420, Springer Verlag, Germany (2005) (Abstract Only).

Ghoreschi, K., et al., "Fumaric acid ester an antipsoriatic drug abolishes the capacity of T cells to induce Th1-mediated autoimmune disease," *Arch. Dermatol. Res.* 294:28, Springer Verlag, Germany (2002) (Abstract Only).

Gielen, A.W., et al., "Expression of T cell immunoglobulin- and mucin-domain-containing molecules-1 and -3 (TIM-1 and -3) in the rat nervous and immune systems," *J. Neuroimmunol.* 164:93-104, Elsevier B.V., Netherlands (2005).

Gijbels, K., et al.,"Administration of Neutralizing Antibodies to Interleukin-6 (IL-6) Reduces Experimental Autoimmune Encephalomyelitis and Is Associated with Elevated Levels of IL-6 Bioactivity in Central Nervous System and Circulation," *Mol. Med.* 1(7):795-805, Molecular Medicine, United States (1995).

Giovannoni, G. and Miller, D.H., "Multiple sclerosis and its treatment," *J. R. Coll. Physicians Lond.* 33(4):315-322, Royal College of Physicians, England (1999).

Guggenmos, J. et al., "Antibody Cross-Reactivity between Myelin Oligodendrocyte Glycoprotein and the Milk Protein Butyrophilin in Multiple Sclerosis," *J. Immunol.* 172:661-668, The American Association of Immunologists, Inc., United States (2004).

Hemmer, B., et al., "Cytokine Phenotype of Human Autoreactive T Cell Clones Specific for the Immunodominant Myelin Basic Protein Peptide (83-99)," *J. Neurosci. Res.* 45:852-862, Wiley-Liss, Inc., United States (1996).

Hintzen, R.Q. and Polman, C.H., "Th-cell modulation in multiple sclerosis," *Immunol. Today* 18(10):507-508, Elsevier/North-Holland Biomedical Press, England (1997).

Hohenegger, M. et al., "Nephrotoxicity of Fumaric Acid Monoethylester (FA ME)," *Advances in Experimental Medicine and Biology* 252:265-272, Kluwer Academic, United States (1989).

Hultgren, B., et al., "Genetic Absence of γ-Interferon Delays but Does Not Prevent Diabetes in NOD Mice," *Diabetes* 45:812-817, American Diabetes Association, United States (1996).

English language excerpt from Hunziker, T. and Schmidli, J., "Is Psoriasis an Autoimmune Disease?" *Therapeutische Umschau* 50:110-113, Dermatologische Klinik der Universität Bern, Switzerland (1993).

Hunziker, T., and Schmidli, J., "Psoriasis, eine Autoimmunkrankheit?" *Therapeutische Umschau* 50:110-113, Dermatologische Klinik der Universität Bern, Switzerland (1993).

Issazadeh, S., et al., "Cytokine production in the central nervous system of Lewis rats with experimental autoimmune encephalomyelitis: dynamics of mRNA expression for interleukin-10, interleukin-12, cytolysin, tumor necrosis factor α and tumor necrosis factor β," *J. Neuroimmunol.* 61:205-212, Elsevier Science B.V, Netherlands (1995).

Issazadeh, S., et al., "Interferon γ, Interleukin 4 and Transforming Growth Factor β in Experimental Autoimmune Encephalomyelitis in Lewis Rats: Dynamics of Cellular mRNA Expression in the Central Nervous System and Lymphoid Cells," *J. Neurosci. Res.* 40:579-590, Wiley-Liss, Inc. United States (1995).

Issazadeh, S., et al., "Cytokines in relapsing experimental autoimmune encephalomyelitis in DA rats: persistent mRNA expression of proinflammatory cytokines and absent expression of interleukin-10 and transforming growth factor-β," *J. Neuroimmunol.* 69:103-115, Elsevier Science B.V., Netherlands (1996).

Issazadeh, S., et al., "Major histocompatibility complex-controlled protective influences on experimental autoimmune encephalomyelitis are peptide specific," *Eur. J. Immunol.* 27:1584-1587, VCH Verlagsgesellschaft mbH, Germany (1997).

Kappos, L., et al., "Efficacy and safety of oral fumarate in patients with relapsing-remitting multiple sclerosis: a multicentre, randomised, double-blind, placebo-controlled phase IIb study," *Lancet* 372:1463-1472, Lancet Publishing Group., England (2008).

(56) References Cited

OTHER PUBLICATIONS

Khademi, M., et al., "Induction of systemic TNFα in Natalizumab-treated multiple sclerosis," *Eur. J. Neural.* 15:309-312, European Federation of Neurological Sciences, England (2008).

Khademi, M., et al., "Reduction of both pro- and anti-inflammatory cytokines after 6 months of interferon beta-1a treatment of multiple sclerosis," *J. Neuroimmunol.* 103:202-210, Elsevier Science B.V., Netherlands (2000).

Khademi, M., et al., "T Cell Ig- and Mucin-Domain-Containing Molecule-3 (TIM-3) and TIM-1 Molecules Are Differentially Expressed on Human Th1 and Th2 Cells and in Cerebrospinal Fluid-Derived Mononuclear Cells in Multiple Sclerosis," *J. Immunol.* 172:7169-7176, The American Association of Immunologists, Inc., United States (2004).

Kiehl, R. and Ionescu, G., "A Defective Purine Nucleotide Synthesis Pathway in Psoriatic Patients," *Acta Derm. Venereol. (Stockh)* 72:253-255, Society for the Publication of Acta Dermato-Venerologica, Sweden (1992).

Kjellén, P., et al., "Genetic influence on disease course and cytokine response in relapsing experimental allergic encephalomyelitis," *Int. Immunol.* 10:333-340, Oxford University Press, England (1998).

Kolbach, D.N. and Nieboer, C., "Fumaric acid therapy in psoriasis: Results and side effects of 2 years of treatment," *J. Am. Acad. Derm.* 27(5):769-771, Mosby, United States (1992).

Krakauer, M., et al., "Dynamic T-lymphocyte Chemokine Receptor Expression Induced by Interferon-beta Therapy in Multiple Sclerosis," *Scand. J. Immunol.* 64:155-163, Blackwell Publishing Ltd., England (2006).

Krakowski, M. and Owens, T., "Interferon-γ confers resistance to experimental allergic encephalomyelitis," *Eur. J. Immunol.* 26:1641-1646, VCH Verlagsgesellschaft mbH, Germany (1996).

Kuroda, K., et al., "Fumaric Acid Enhances DNA Synthesis of Rat Hepatocytes by Counteracting the Toxicities of Mitomycin C and Aflatoxin $B_1$," *Jpn. J. Cancer Res. (Gann)* 77:750-758, Japanese Cancer Association, Japan (1986).

Lafaille, J.J., et al., "Myelin Basic Protein-specific T Helper 2 (Th2) Cells Cause Experimental Autoimmune Encephalomyelitis in Immunodeficient Hosts Rather than Protects Them from the Disease," *J. Exp. Med.* 186(2):307-312, The Rockefeller University Press, United States (1997).

Lafaille, J.J., "The Role of Helper T Cell Subsets in Autoimmune Diseases," *Cytokine & Growth Factor Rev.* 9(2):139-151, Elsevier Science Ltd., England (1998).

Lahti, A. and Maibach, H.I., "Contact urticaria from diethyl fumarate," *Contact Dermatitis* 12:139-140, Munksgaard, Denmark (1985).

Laman, J.D., et al., "Balancing the Th1/Th2 concept in multiple sclerosis," *Immunol. Today* 19(11):489-490, Elsevier/North-Holland Biomedical Press, England (1998).

Lehnert, S., et al., "Radiation Response of Drug-Resistant Variants of a Human Breast Cancer Cell Line: The Effect of Glutathione Depletion," *Radiation Res.* 124:208-215, Academic Press, Inc., United States (1998).

Liedtke, W., et al., "Effective Treatment of Models of Multiple Sclerosis by Matrix Metalloproteinase Inhibitors," *Ann. Neurol.* 44(1):35-46, The American Neurological Association, United States (1998).

Link, J. et al., "Organ-specific autoantigens induce interferon-γ and interleukin-4 mRNA expression in mononuclear cells in multiple sclerosis and myasthenia gravis," *Neurology* 44:728-734, The American Academy of Neurology, United States (1994).

Link, J., et al., "Organ-specific Autoantigens Induce Transforming Growth Factor-β mRNA Expression in Mononuclear Cells in Multiple Sclerosis and Myasthenia Gravis," *Annals Neurol.* 35:197-203, The American Neurological Association, United States (1994).

Link, J., et al., "Optic neuritis is associated with myelin basic protein and proteolipid protein reactive cells producing interferon-γ, interleukin-4 and transforming growth factor-β," *J. Neuroimmunol.* 49:9-18, Elsevier Science B.V., Netherlands (1994).

Link, J., et al., "Increased Transforming Growth Factor-β, Interleukin-4, and Interferon-γ in Multiple Sclerosis," *Ann. Neurol.* 36(3):379-386, The American Neurological Association, United States (1994).

Link, H., "The cytokine storm in multiple sclerosis," *Mult. Scler.* 4:12-15, Stockton Press, England (1998).

Linker, R.A., et al., "Fumarates for the treatment of multiple sclerosis: potential mechanisms of action and clinical studies," *Expert Rev. Neurother.* 8(11):1683-1690, Expert Reviews Ltd., England (2008).

Lobell, A., et al., "Suppressive DNA Vaccination in Myelin Oligodendrocyte Glycoprotein Peptide-Induced Experimental Autoimmune Encephalomyelitis Involves a T1-Biased Immune Response," *J. Immunol.* 170:1806-1813, The American Association of Immunologists, Inc., United States (2003).

Lobell, A., et al., "Vaccination with DNA Encoding an Immunodominant Myelin Basic Protein Peptide Targeted to Fc of Immunoglobulin G Suppresses Experimental Autoimmune Encephalomyelitis," *J. Exp. Med.* 187(9):1543-1548, The Rockefeller University Press, United States (1998).

Lopez, E., et al., "Interferon γ, IL2, IL4, IL10 and TNFα Secretions in Multiple Sclerosis Patients Treated with an Anti-CD4 Monoclonal Antibody," *Autoimmunity* 29:87-92, OPA (Overseas Publishers Association) N.V., England (1999).

Lorentzen, J.C., et al., "Genetic analysis of inflammation, cytokine mRNA expression and disease course of relapsing experimental autoimmune encephalomyelitis in DA rats," *J. Neuroimmunol.* 80:31-37, Elsevier Science N.V., Netherlands (1997).

Lorentzen, J.C., et al., "Protracted, relapsing and demyelinating experimental autoimmune encephalomyelitis in DA rats immunized with syngeneic spinal cord and incomplete Freund's adjuvant," *J. Neuroimmunol.* 63:193-205, Elsevier Science B.V., Netherlands (1995).

Lyons, J.-A., et al., "Pathogenesis of acute passive murine encephalomyelitis II. Th 1 phenotype of the inducing population is not sufficient to cause disease," *J. Neuroimmunol.* 93:26-36, Elsevier Science B.V., Netherlands (1999).

Määttä., J.A., et al., "Neutrophils secreting tumor necrosis factor alpha infiltrate the central nervous system of BALB/c mice with experimental autoimmune encephalomyelitis," *J. Neuroimmunol.* 90:162-175, Elsevier Science B.V., Netherlands (1998).

Martin, R., et al., "T helper cell differentiation in multiple sclerosis and sutoimmunity," *Immunol. Today* 19(11):495-498, Elsevier Science, England (1998).

Mattner, F., et al., "Inhibition of Th1 development and treatment of chronic-relapsing experimental allergic encephalomyelitis by a non-hypercalcemic analogue of 1,25-dihydroxyvitamin in $D_3$," *Eur. J. Immunol.* 30:498-508, Wiley-VCH Verlag GmbH, Germany (2000).

Matusevicius, D., et al., "Autoantigen-induced IL-13 mRNA expression is increased in blood mononuclear cells in myasthenia gravis and multiple sclerosis," *Eur. J. Neurol.* 4:468-475, Rapid Science Publishers, England (1997).

Asadullah, K., et al., "Influence of monomethylfumarate on monocytic cytokine formation—explanation for adverse and therapeutic effects in psoriasis?" *Arch. Dermatol. Res.* 289:623-630, Springer-Verlag, Germany (1997).

Bacharach-Buhles, M., et al., "The Effect of Fumaric Acid Esters and Dithranol on Acanthosis and Hyperproliferation in Psoriasis Vulgaris," *Acta Derm. Venereol. (Stockh)* 76:190-193, Scandinavian University Press, Sweden (1996).

Balashov, K.E., et al., "Increased interleukin 12 production in progressive multiple sclerosis: Induction by activated $CD4_+$ T cells via CD40 ligand," *Proc. Natl. Acad. Sci. USA* 94:599-603, The National Academy of Sciences of the United States of America, United States (1997).

Barcia, C., et al., "Parkinson's Disease and Inflammatory Changes," *Neurotox. Res.* 5(6):411-418, FP Graham Publishing Co., United States (2003).

Breuer, K., et al., "Therapy of noninfectious granulomatous skin diseases with fumaric acid esters," *Br. J. Dermatol.* 152:1290-1295, British Association of Dermatologists, England (2005).

Eberlein-König, B., et al., "Disseminated Granuloma Annulare—Treatment with Fumaric Acid Esters," *Dermatology* 210:223-226, S. Karger AG, Switzerland (2005).

(56) References Cited

OTHER PUBLICATIONS

Link, H., et al., "Virus-reactive and autoreactive T cells are accumulated in cerebrospinal fluid in multiple sclerosis," *J. Neuroimmunol.* 38:63-74, Elsevier Science Publishers B.V., Netherlands (1992).
Litjens, N.H.R., et al., "Monomethylfumarate affects polarization of monocyte-derived dendritic cells resulting in down-related Th1 lymphocyte responses," *Eur. J. Immunol.* 34:565-575, Wiley-VCH Verlag GmbH & Co. KGaA, Germany (2004).
Litjens, N.H.R., et al., "Pharmacokinetics of oral fumarates in healthy subjects," *Br. J. Clin. Pharmacol.* 58(4):429-432, Blackwell Publishing Ltd, England (2004).
Lobell, A., et al., "Presence of CpG DNA and the Local Cytokine Milieu Determine the Efficacy of Suppressive DNA Vaccination in Experimental Autoimmune Encephalomyelitis," *J. Immunol.* 136:4754-4762, The American Association of Immunologists, United States (1999).
Loewe, R., et al., "Dimethylfumarate Inhibits TNF-Induced Nuclear Entry of NF-κB/p65 in Human Endothelial Cells," *J. Immunol.* 168:4781-4787, The American Association of Immunologists, United States (2002).
Mayne, M., et al., "Antisense Oligodeoxynucleotide Inhibition of Tumor Necrosis Factor-α Expression Is Neuroprotective After Intracerebral Hemorrhage," *Stroke* 32:240-248, American Heart Association, Inc., United States (2001).
McGeer, P.L., et al., "Expression of the histocompatibility glycoprotein HLA-DR in neurological disease," *Acta Neuropathol.* 76:550-557, Springer-Verlag, Germany (1988).
Muhallab, S., et al., "Intra-CNS activation by antigen-specific T lymphocytes in experimental autoimmune encephalomyelitis," *J. Neuroimmunol.* 113:202-211, Elsevier Science B.V., Netherlands (2001).
Mustafa, M.I., et al., "T cell immunity and interferon-γ secretion during experimental allergic encephalomyelitis in Lewis rats," *J. Neuroimmunol.* 31:165-177, Elsevier Science Publishers B.V., Netherlands (1991).
Mustafa, M., et al., "Immunopharmacologic Modulation of Experimental Allergic Encephalomyelitis: Low-Dose Cyclosporin-A Treatment Causes Disease Relapse and Increased Systemic T and B Cell-Mediated Myelin-Directed Autoimunity," *Scand. J. Immunol.* 38:499-507, Blackwell Scientific Publications, England (1993).
Mustafa, M., et al., "The major histocompatibility complex influences myelin basic protein 63-88-induced T cell cytokine profile and experimental autoimmune encephalomyelitis," *Eur. J. Immunol.* 23:3089-3095, VCH Verlagsgesellschaft mbH, Germany (1993).
Mustafa, M., et al., "Protective Influences on Experimental Autoimmune Encephalomyelitis by MHC Class I and Class II Alleles," *J. Immunol.* 153:3337-3344, The American Association of Immunologists, United States (1994).
Navikas, V., et al., "Increased mRNA Expression of IL-10 in Mononuclear Cells in Multiple Sclerosis and Optic Neuritis," *Scand. J. Immunol.* 41:171-178, Blackwell Scientific Publications, England (1995).
Navikas, V., et al., "Augmented expression of tumor necrosis factor-α and lymphotoxin in mononuclear cells in multiple sclerosis and optic neuritis," *Brain* 119:213-223, Oxford University Press, England (1996).
Nibbering, P.H. et al., "Effects of Monomethylfumarate on Human Granulocytes," *J. Invest. Dermatol.* 101:37-42, The Society for Investigative Dermatology, Inc., United States (1993).
Nibbering, P.H., et al., "Intracellular signalling by binding sites for the antipsoriatic agent monomethylfumarate on human granulocytes," *Br. J. Dermatol.* 137:65-75, British Association of Dermatologists, England (1997).
Nieboer, C., et al., "Systemic therapy with fumaric acid derivates: New possibilities in the treatment of psoriasis," *J. Am. Acad. Dermatol.* 20:601-608, Mosby, United States (1989).
Ockenfels, H.M., et al., "The antipsoriatic agent dimethylfumarate immunomodulates T-cell cytokine secretion and inhibits cytokines of the psoriatic cytokine network," *Br. J. Dermatol.* 139:390-395, British Association of Dermatologists, England (1998).

Olsson, T., et al., "Autoreactive T Lymphocytes in Multiple Sclerosis Determined by Antigen-induced Secretion of Interferon-γ," *J. Clin. Invest.* 86:981-985, The American Society for Clinical Investigation, Inc., United States (1990).
Olsson, T., "Cytokines in neuroinflammatory disease: role of myelin autoreactive T cell production of interferon-gamma," *J. Neuroimmunol.* 40:211-218, Elsevier Science Publishers B.V., Netherlands (1992).
Olsson, T., et al., "Increased numbers of T cells recognizing multiple myelin basic protein epitopes in multiple sclerosis," *Eur. J. Immunol.* 22:1083-1087, VCH Verlagsgesellschaft mbH, Germany (1992).
Olsson, T., "Cerebrospinal Fluid," *Ann. Neurol.* 36:S100-S102, American Neurological Association, United States (1994).
Olsson, T., "Role of cytokines in multiple sclerosis and experimental autoimmune encephalomyelitis," *Eur. J. Neurol.* 1:7-19, Rapid Communications of Oxford Ltd., England (1994).
Olsson, T., "Cytokine-producing cells in experimental autoimmune encephalomyelitis and multiple sclerosis," *Neurology* 45(Suppl 6):S11-S15, Lipincott Williams & Wilkins, United States (1995).
Olsson, T., et al. "Genetics of rat neuroinflammation," *J. Neuroimmunol.* 107:191-200, Elsevier Science B.V., Netherlands (2000).
Olsson, T., et al., "Depletion of Vβ5.2/5.3 T cells with a humanized antibody in patients with multiple sclerosis," *Eur. J. Neurol.* 9:153-164, European Federation of Neurological Societies, England (2002).
Olsson, T., et al., "Harm or heal—divergent effects of autoimmune neuroinflammation?" *TRENDS in Immunol.* 24(1):5-6, Elsevier Science Ltd., England (2003).
Panitch, H.S., et al., "Exacerbations Of Multiple Sclerosis In Patients Treated With Gamma Interferon," *Lancet* 329:893-895, Lancet Publishing Group, England (1987).
Pereira, M.A., et al., "Use of azoxymethane-induced foci of aberrant crypts in rat colon to identify potential cancer chemopreventive agents," *Carcinogenesis* 15(5):1049-1054, Oxford University Press, England (1994).
Pette, M., et al., "Differential effects of phosphodiesterase type 4-specific inhibition on human autoreactive myelin-specific T cell clones," *J. Neuroimmunol.* 98:147-156, Elsevier Science B.V., Netherlands (1999).
Prochaska, H.J., et al., "Oltipraz, an inhibitor of human immunodeficiency virus type 1 replication," *Proc. Natl. Acad. Sci. USA* 90(9):3953-3957, National Academy of Sciences, United States (1993).
Prochaska, H.J., et al., "Elevation of Glutathione Levels by Phase II Enzyme Inducers: Lack of Inhibition of Human Immunodeficiency Virus Type 1 Replication in Chronically Infected Monocytoid Cells," *Mol. Pharmacol.* 45:916-921, The American Society for Pharmacology and Experimental Therapeutics, United States (1994).
Rao, C.V., et al., "Chemoprevention of Azoxymethane-Induced Colon Cancer by Ascorbylpalmitate, Carbenoxolone, Dimethylfumarate and *p*-Methoxyphenol in Male F344 Rats," *Anticancer Res.* 15:1199-1204, Anticancer Research, Greece (1995).
Rao., K.S. and Mishra, S.H., "Antihepatotoxic activity of monomethyl fumarate isolated from *Fumaria indica*," *J. Ethnopharmacol.* 60:207-213, Elsevier Science Ireland Ltd., Ireland (1998).
Ristori, G., et al., "T cell response to myelin basic protein before and after treatment with interferon beta in multiple sclerosis," *J. Neuroimmunol.* 99:91-96, Elsevier Science B.V., Netherlands (1999).
Robinson, W.H., et al., "Protein microarrays guide tolerizing DNA vaccine treatment of autoimmune encephalomyelitis," *Nat. Biotechnol.* 21(9):1033-1039, Nature Publishing Group, United States (2003).
Rohowsky-Kochan, C., et al., "Impaired interleukin-12 production in multiple sclerosis patients," *Mult. Scler.* 5:327-334, Stockton Press, England (1999).
Rohowsky-Kochan, C., et al., "Cytokine secretion profile of myelin basic protein-specific T cells in multiple sclerosis," *Mult. Scler.* 6:69-77, Macmillan Publishers Ltd., England (2000).
Romagnani, S., "The Th1/Th2 paradigm," *Immunol. Today* 18(6):263-266, Elsevier Science Ltd., England (1997).

(56) References Cited

OTHER PUBLICATIONS

Rook, G.A.W., et al., "Bacterial vaccines for the treatment of multiple sclerosis and other autoimmune diseases," *Immunol. Today* 21(10):503-508, Elsevier Science Ltd., England (2000).

Samoilova, E.B., et al., "Experimental Autoimmune Encephalomyelitis in Intercellular Adhesion Molecule-1-Deficient Mice," *Cell. Immunol.* 190:83-89, Academic Press, United States (1998).

Sebök, B., et al., "Antiproliferative and cytotoxic profiles of antipsoriatic fumaric acid derivatives in keratinocyte cultures," *Eur. J. Pharmacol.* 270:79-87, Elsevier Science B.V., Netherlands (1994).

Sebök, B., et al., "Effect of Fumaric Acid, Its Dimethylester, and Topical Antipsoriatic Drugs on Epidermal Differentiation in the Mouse Tail Model," *Skin Pharmacol.* 9:99-103, S. Karger AG, Switzerland (1996).

Singh, V.K., et al., "The Paradigm of Th1 and Th2 Cytokines. Its Relevance to Autoimmunity and Allergy," *Immunol. Res.* 20:147-161, Humana Press Inc., United States (1999).

Sinigaglia, F., et al., "Type 1 interferons and the Th1/Th2 paradigm," *Dev. Comp. Immunol.* 23:657-663, Elsevier Science Ltd., United States (1999).

Smeltz, R.B. and Swanborg, R.H., "Concordance and Contradiction Concerning Cytokines and Chemokines in Experimental Demyelinating Disease," *J. Neurosci. Res.* 51:147-153, Wiley-Liss, Inc., United States (1998).

Söderström, M., et al., "T Cells Recognizing multiple Peptides of Myelin Basic Protein are Found in Blood and Enriched in Cerebrospinal Fluid in Optic Neuritis and Multiple Sclerosis," *Scand. J. Immunol.* 37:355-368, Blackwell Scientific Publications, England (1993).

Spencer, S.R., et al., "Induction of Glutathione Transferases and NAD(P)H:Quinone Reductase by Fumaric Acid Derivatives in Rodent Cells and Tissues," *Cancer Res.* 50:7871-7875, American Association for Cancer Research, United States (1990).

Su, J.Y.C., et al., "Reduction of $H_2O_2$-evoked, intracellular calcium increases in the rat N18-RE-105 neuronal cell line by pretreatment with an electrophilic antioxidant inducer," *Neurosci. Lett.* 273:109-112, Elsevier Science Ireland Ltd., Ireland (1999).

Sun, J.-B., et al., "Treatment of experimental autoimmune encephalomyelitis by feeding myelin basic protein conjugated to cholera toxin B subunit," *Proc. Natl. Acad. Sci. USA* 93:7196-7201, National Academy of Sciences, United States (1996).

Thio, H.B., et al., "Fumaric acid derivatives evoke a transient increase in intracellular free calcium concentration and inhibit the proliferation of human keratinocytes," *Brit. J. Dermatol.* 131:856-861, Blackwell Scientific Publications, England (1994).

Venten, I., et al., "Treatment of Therapy-Resistant Alopecia Areata With Fumaric Acid Esters," *Eur. J. Med. Res.* 11:300-305, I. Holzapfel Publishers, Germany (Jul. 2006).

Wallström, E., et al., "Memantine abrogates neurological deficits, but not CNS inflammation, in Lewis rat experimental autoimmune encephalomyelitis," *J. Neurol. Sci.* 137:89-96, Elsevier Science B.V., Netherlands (1996).

Wallström, E., et al., "Increased reactivity to myelin oligodendrocyte glycoprotein peptides and epitope mapping in HLA DR2(15)—multiple sclerosis," *Eur. J. Immunol.* 28:3329-3335, Wiley-VCH Verlag GmbH, Germany (1998).

Wang, W.Z., et al. "Myelin antigen reactive T cells in cerebrovascular diseases," *Clin. Exp. Immunol.* 88:157-162, Blackwell Scientific Publications, England (1992).

Weissert, R., et al., "Protective DNA vaccination against organ-specific autoimmunity is highly specific and discriminates between single amino acid substitutions in the peptide autoantigen," *Proc. Natl. Acad. Sci. USA* 97(4):1689-1694, National Academy of Sciences, United States (2000).

Wright, R., "Autoimmune disease of the gastro-intestinal tract," *Postgrad. med. J.* 44:765-768, BMJ Publishing Group, England (1968).

Zhu, J., et al., "Cytokine production and the pathogenesis of experimental autoimmune neuritis and Guillain-Barré syndrome," *J. Neuroimmunol.* 84:40-52, Elsevier Science B.V., Netherlands (1998).

Zipp, F., "No Evidence for Generation of Th-2-like MBP-Specific T-Cell Lines by Blockade of the Costimulatory Molecule B7-1," *Scand J. Immunol.* 52:510-514, Blackwell Science Ltd., England (2000).

Alexander, A. and Wong, S., "Graft Versus Host Disease—Pathophysiology & Management," *Jacksonville Medicine: Bone Marrow Transplantation* 51(11):1-7, Duval County Medical Society Foundation for the Duval, Clay, Nassau, St. Johns & Putnam Medical Societies, United States (2000).

Anderson, J., et al., "Aetiology of Multiple Sclerosis," *Br. Med. J* 1(5433):466-467, British Medical Association, England (1965).

Brochet, B., "[Non-specific immunosuppression and multiple sclerosis]," *Rev. Neurol.* (Paris) 154(8-9):629-634, Masson, France (1998) (Abstract Only).

Calabrese, V., et al., "Acetylcarnitine Induces Heme Oxygenase in Rat Astrocytes and Protects Against Oxidative Stress: Involvement of the Transcription Factor Nrf2," *J. Neurosci. Res.* 79:509-521, Wiley-Liss, Inc., United States (2005).

Chen, X.-L. and Kunsch, C., "Induction of Cytoprotective Genes Through Nrf2/Antioxidant Response Element Pathway: A New Therapeutic Approach for the Treatment of Inflammatory Diseases," *Curr. Pharm. Des.* 10:879-891, Bentham Science Publishers Ltd., Netherlands (2004).

Coras, B., et al., "Fumaric acid esters therapy: a new treatment modality in pityriasis rubra pilaris?" *Br. J Dermatol.* 152:388-389, British Association of Dermatologists, England (2005).

Fox, R.J., "BG00012—A Novel Oral Therapy in Development for the Treatment of Multiple Sclerosis," *European Neurological Review* 3(1):99-103, Touch Briefings, England (2008).

Gambichler, T., et al., "Clearance of Necrobiosis lipoidica with Fumaric Acid Esters," *Dermatology* 207(4):422-424, S. Karger AG, Switzerland (2003).

Gao, L., et al., "Novel N-3 Fatty Acid Oxidation Products Activate Nrf2 By Destabilizing The Association Between Keap1 and Cullin3," *J Biol. Chem.* M607622200, 18 pages, The American Society for Biochemistry and Molecular Biology, Inc., United States (Nov. 2006).

Gilgun-Sherki, Y., et al., "The role of oxidative stress in the pathogenesis of multiple sclerosis: The need for effective antioxidant therapy," *J. Neurol.* 251:261-268, Springer-Verlag, Germany (2004).

Graves, M.C., et al., "Inflammation in amyotrophic lateral sclerosis spinal cord and brain is mediated by activated macrophages, mast cells and T cells," *Amyotroph. Lateral Scler. Other Motor Neuron Disord.* 5:213-219, Martin Dunitz, England (2004).

Hagedorn, M., et al., "Therapie der rezidivierenden benignen Aphthosis mit Fumarsäureestern," *Akt. Dermatol.* 31:383-387, Georg Thieme Verlag KG, Germany (2005) (Abstract Only in English).

Kensler, T.W., et al., "Cell Survival Responses to Environmental Stresses Via the Keap1-Nrf2-ARE Pathway," *Annu. Rev. Pharmocol. Toxicol.* 47:6.1-6.28, Annual Reviews, United States (2007; Epub August 2006).

Kreuter, A., et al., "Treatment of disseminated granuloma annulare with fumaric acid esters," *BMC Dermatol.* 2(5):1-4, BioMed Central Ltd., England (2002).

Kreuter, A., et al., "Fumaric acid esters in necrobiosis lipoidica: results of a prospective noncontrolled study," *Br. J. Dermatol.* 153:802-807, British Association of Dermatologists, England (2005).

Kwak, M.-K., et al., "Enhanced Expression of the Transcription Factor Nrf2 by Cancer Chemopreventive Agents: Role of Antioxidant Response Element-Like Sequences in the *nrf2* Promoter," *Mol. Cell Biol.* 22(9):2883-2892, American Society for Microbiology, United States (2002).

Kwak, M.-K., et al., "Modulation of Gene Expression by Cancer Chemopreventive Dithiolethiones through the Keap1-Nrf2 Pathway," *J. Biol. Chem.* 278(10):8135-8145, The American Society for Biochemistry and Molecular Biology Inc., United States (2003).

(56) References Cited

OTHER PUBLICATIONS

Lahti, A., et al., "Acetylsalicylic acid inhibits non-immunologic contact urticaria," *Contact Dermatitis* 16:133-135, Munksgaard International Publishers Ltd., Denmark (1987).
Lee, J.-M., et al., "Identification of the NF-E2-related Factor-2-dependent Genes Conferring Protection against Oxidative Stress in Primary Cortical Astrocytes Using Oligonucleotide Microarray Analysis," *J. Biol. Chem.* 278(14):12029-12038, The American Society for Biochemistry and Molecular Biology, Inc., United States (2003).
Lehmann, J.C.U., et al., "Dimethylfumarate Induces Immunosuppression via Gluthione Depletion and Subsequent Induction of Heme Oxygenase 1," *J. Invest. Dermatol.* 127:835-845, The Society for Investigative Dermatology, United States (Epub Jan. 18, 2007).
Liang, Q., et al., "Noninvasive, Repetitive, Quantitative Measurement of Gene Expression from a Bicistronic Message by Positron Emission Tomography, Following Gene Transfer with Adenovirus," *Mol. Ther.* 6(1):73-82, The American Society of Gene Therapy, United States (2002).
Luker, G.D., et al., "Noninvasive Bioluminescence Imaging of Herpes Simplex Virus Type I Infection and Therapy in Living Mice," *J. Virol.* 76(23):12149-12161, American Society for Microbiology, United States (2002).
Ma, Q., et al., "Multiorgan Autoimmune Inflammation, Enhanced Lymphoproliferation, and Impaired Homeostasis of Reactive Oxygen Species in Mice Lacking the Antioxidant-Activated Transcription Factor *Nrf2*," *Am. J. Pathol.* 168(6):1960-1974, American Society for Investigative Pathology, United States (Jun. 2006).
Mattson, M.P. and Cheng, A., "Neurohormetic phytochemicals: low-dose toxins that induce adaptive neuronal stress responses," *TRENDS in Neurosciences* 29(11):632-639, Elsevier Ltd., England (Sep. 2006).
Nguyen, T., et al., "Nrf2 Controls Constitutive and Inducible Expression of ARE-driven Genes through a Dynamic Pathway Involving Nucleocytoplasmic Shuttling by Keap1," *J. Biol, Chem.* 280(37):32485-32492, The American Society for Biochemistry and Molecular Biology, Inc, United States (2005).
Nieboer, C., et al., "Fumaric Acid Therapy in Psoriasis: A Double-Blind Comparison between Fumaric Acid Compound Therapy and Monotherapy with Dimethylfumaric Acid Ester," *Dermatologica* 181:33-37, Karger AG, Switzerland (1990).
Nowack, U., et al., "Successful treatment of recalcitrant cutaneous sarcoidosis with fumaric acid esters," *BMC Dermatol.* 2(15):1-5, BioMed Central Ltd., England (2002).
O'Garra, A., et al., "CD4+ T-cell subsets in autoimmunity." *Curr. Opin. Immunol.* 9:872-883, Current Biology Ltd., England (1997).
Olsson, T., et al., "Chapter 22: MHC and Non-MHC Genetics of Experimental Autoimmune Encephalomyelitis," in *From Basic Immunology to Immune-Mediated Demyelination*, Martino, G. and Adorini, L., eds., p. 246-264, Springer-Verlag, Italy (1999).
Olsson, T., "Critical Influences of the Cytokine Orchestration on the Outcome of Myelin Antigen-Specific T-Cell Autoimmunity in Experimental Autoimmune Encephalomyelitis and Multiple Sclerosis," *Immunol. Rev.* 144:245-268, Munksgaard, Denmark (1995).
Pashenkov, M., et al., "Recruitment of dendritic cells to the cerebrospinal fluid in bacterial neuroinfections," *J. Neuroimmunol.* 122:106-116, Elsevier Science B.V., Netherlands (2002).
Permana, P.A., et al., "Macrophage-secreted factors induce adipocyte inflammation and insulin resistance," *Biochem. Biophys. Res. Commun.* 341:507-514, Elsevier Inc., United States (Epub Jan. 2006).
Pette, M., et al., "In vitro modulation of human, autoreactive MBP-specific CD4 + T-cell clones by cyclosporin A," *J. Neuroimmunol.* 76:91-99, Elsevier Science B.V., Netherlands (1997).
Roodnat, J.I., et al.,"Akute Niereninsuffizienz bei der Behandlung der Psoriasis mit Fumasäure-Estern," *Schweiz. med. Wschr.* 119:826-830, Basel, B. Schwabe & Co., Switzerland (1989) (Abstract Only in English).
Rudge, P., "Cyclosporine and multiple sclerosis: The cons," *Neurology* 38(7)(Suppl 2):29-30, Lippincott Williams & Wilkins, United States (1988).
Ruuls, S.R., et al., "The Length of Treatment Determines Whether IFN-β Prevents or Aggravates Experimental Autoimmune Encephalomyelitis in Lewis Rats," *J. Immunol.* 157:5721-5731, The American Association of Immunologists, United States (1996).
Satoh, T., et al., "Activation of the Kcap1/Nrf2 pathway for neuroprotection by electrophillic phase II inducers," *Proc. Natl. Acad. Sci. USA* 103(3):768-773, The National Academy of Sciences of the USA, United States (Jan. 2006).
Schilling, F. and Schopf, R.E., "Adultes Debré-de Toni-Fanconi-Syndrom mit Osteomalazie, erworben durch Langzeittherapie einer Psoriasis mit Fumarsäureester-zugleich ein Beitrag zur malazischen Osteoarthropathie," *Akt. Rheumatol.* 24(6):174-179, Georg Thieme Verlag, Germany (1999)(Abstract Only in English).
Schilling, S., et al., "Fumaric acid esters are effective in chronic experimental autoimmune encephalomyelitis and suppress macrophage infiltration," *Clin. Exp. Immunol.* 145:101-107, British Society for Immunology, England (2006).
Schwinghammer, T.L. and Bloom, E.J., "Pharmacologic prophylaxis of acute graft-versus-host disease after allogeneic marrow transplantation," *Clinical Pharm.* 12:736-761, American Society of Hospital Pharmacists, Inc., United States (1993).
Shih, A.Y., et al., "A Small-Molecule-Inducible Nrf2-Mediated Antioxidant Response Provides Effective Prophylaxis against Cerebral Ischemia In Vivo," *J. Neurosci.* 25(44):10321-10335, Society for Neuroscience, United States (2005).
Summers, S.A., "Ceramides in insulin resistance and lipotoxicity," *Prog. Lipid Res.* 45:42-72, Elsevier Ltd., England (Jan. 2006: Epub Dec. 2005).
Thimmulappa, R.K., et al., "Nrf2 is a critical regulator of the innate immune response and survival during experimental sepsis," *J. Clin. Invest.* 116(4):984-995, American Society for Clinical Investigation, United States (Apr. 2006).
Van Horssen, J., et al., "NAD(P)H:quinone oxidoreductase 1 expression in multiple sclerosis lesions," *Free Radic. Biol. Med.* 41:311-317, Elsevier Inc., United States (Epub Apr. 2006).
Van Loenen, A.C., et al., "Fumaarzuurtherapie: van fictie tot werkelijkheid?" *Pharm. Weekbl.* 124:894-900, D B Centens Witgeversmij, Netherlands (1989) (Abstract Only in English).
Vandermeeren, M., et al., "Dimethylfumarate Is an Inhibitor of Cytokine-Induced E-Selection, VCAM-1, and ICAM-1 Expression in Human Endothelial Cells," *Biochem. Biophys. Res. Comm.* 234:19-23, Academic Press, United States (1997).
Vandermeeren, M., et al., "Dimethylfumarate is an Inhibitor of Cytokine-Induced Nuclear Translocation of NF-κB1, But Not Rc1A in Normal Human Dermal Fibroblast Cells," *J. Inves. Dermatol.* 116:124-130, The Society for Investigative Dermatology, Inc., United States (2001).
Wakabayashi, N., et al., "*Keap1*-null mutation leads to postnatal lethality due to constitutive Nrf2 activation," *Nat. Genet.* 35(3):238-245, Nature Publishing Group, United States (2003).
Wanscher, B. and Sørensen, P.S., "Nye behandlingsmuligheder for dissemineret sklerose?" *Ugeskr Læger* 156(43):6353-6358, Den Alm Danske Laegerforening, Denmark (1994) (Abstract Only in English).
Werdenberg, D., et al., "Presystemic Metabolism and Intestinal Absorption of 1 Antipsoriatic Fumaric Acid Esters," *Biopharm. Drug Dispos.* 24(6):259-273, John Wiley & Sons, Ltd., England (2003).
Werdenberg, D., *Stability, Permeability and Pharmacokinetics of Perorally Administered Fumarates*, Doctoral Dissertation submitted to the Swiss Federal Institute of Technology Zurich, pp. 86, 87, 90, 125 (2003).
Zhu, K. and Mrowietz, U., "Inhibition of Dendritic Cell Differentiation by Fumaric Acid Esters," *J. Invest. Dermatol.* 116:203-208, The Society for Investigative Dermatology, Inc., United States (2001).
The Lenercept Multiple Sclerosis Study Group and the University of British Columbia MS/MRI Analysis Group, "TNF neutralization in MS: Results of a randomized, placebo-controlled multicenter study," *Neurol.* 53:457-465, American Academy of Neurology, United States (1999).

(56) References Cited

OTHER PUBLICATIONS

"Oral Compound BG-12 Achieves Primary Endpoint in Phase II Study of Relapsing-Remitting Multiple Sclerosis; Treatment with BG-12 Led to Statistically Significant Reductions in MRI Measures," Biogen Idec, accessed at http://phx.corporate-ir.net/staging/phoenix.zhtml?c=148682?p=irol-newsArticle_printd &ID=861749?highlight, published online May 30, 2006, 2 pages.

"Phase II Study of Oral Compound BG-12 Meets Primary Endpoint in Multiple Sclerosis," Biogen Idec, accessed at http://phx.corporate-ir.net/staging/phoenix.zhtml?c=148682?p=irol-newsArticle_print?ID=801882?highlight, published online Jan. 9, 2006, 1 page.

"Polyarthritis," Wikipedia.org, accessed at www.en.wikipedia.org/wiki/Polyarthritis, accessed on Sep. 3, 2008, 4 pages.

*Immunmodulation durch Fumaderm. Das richtungsweisende Konzept*, Charite-Berlin Hautklinik Symposium, Nov. 1-3, 1996, p. 1-27.

Partial English language translation, 4 pages, of *Immunmodulation durch Fumaderm. Das richtungsweisende Konzept*, Charite-Berlin Hautklinik Symposium, Nov. 1-3, 1996, p. 1-27.

Ando, D.G., et al., "Encephalitogenic T Cells in the B10.PL Model of Experimental Allergic Encephalomyelitis (EAE) Are of the Th-1 Lymphokine Subtype," *Cell. Immunol.* 124:132-143, Academic Press, Inc., United States (1989).

Baker, D., et al., "Induction of chronic relapsing experimental allergic encephalomyelitis in Biozzi mice," *J. Neuroimmunol.* 28(3):261-270, Elsevier Science Publishers B.V. (Biomedical Division), Netherlands, (1990).

Baxter, A.G., et al., "High and Low Diabetes Incidence Nonobese Diabetic (NOD) Mice: Origins and Characterisation," *Autoimmunity* 9:61-67, Harwood Academic Publishers GmbH, England (1991).

Bayard, W., et al., "Perorale Langzeitbehandlung der Psoriasis mit Fumarsäurederivaten" *Hautarzt* 38:279-285, Springer-Verlag, Germany (1987) (Abstract Only in English).

Ben-Nun, A., et al., "The rapid isolation of clonable antigen-specific T lymphocyte lines capable of mediating autoimmune encephalomyelitis," *Eur. J. Immunol.* 11:195-199, Verlag Chemie, GmbH, Germany (1981).

Butter, C., et al., "Mononuclear cell trafficking and plasma protein extravasation into the CNS during chronic relapsing experimental allergic encephalomyelitis in Biozzi AB/H mice," *J. Neurol. Sci.* 104:9-12, Elsevier Science Publishers B.V., Netherlands (1991).

Dinkova-Kostova, A.T., et al., "Potency of Michael reaction acceptors as inducers of enzymes that protect against carcinogenesis depends on their reactivity with sulfhydryl groups," *Proc. Natl. Acad. Sci. USA* 98(6):3404-3409, National Academy of Sciences, United States (2001).

*Encyclopedia of Molecular Biology and Molecular Medicine*, Meyers, R.A., ed., p. 343, VCH Verlagsgesellschaft mbH, Germany (1996).

Ercolini, A.M. and Miller, S.D., "Mechanisms of Immunopathology in Murine Models of Central Nervous System Demyelinating Disease," *J. Immunol* 176(6):3293-3298, The American Association of Immunologists, Inc., United States (Mar. 2006).

Eugster, H.-P., et al., "Severity of symptoms and demyelination in MOG-induced EAE depends on TNFR1," *Eur. J. Immunol.* 29:626-632, Wiley-VCH Verlag GmbH, Germany (1999).

Freireich, E.J., et al., "Quantitative Comparison Of Toxicity Of Anticancer Agents In Mouse, Rat, Hamster, Dog, Monkey, and Man," *Cancer Chemother. Reports* 50(4):219-244, National Cancer Institute, United States (1966).

Friedrich, M., et al., "Addition of Pentoxifylline Could Reduce the Side Effects of Fumaric Acid Esters in the Treatment of Psoriasis," *Acta Derm. Venereol.* 81:429-430, Taylor & Francis, Sweden (2001).

Gold, R., et al., "Understanding pathogenesis and therapy of multiple sclerosis via animal models: 70 years of merits and culprits in experimental autoimmune encephalomyelitis research," *Brain* 129:1953-1971, Oxford University Press, England (Aug. 2006)

Habig, W.H., et al., "Glutathione S-Transferases: The First Enzymatic Step in Mercapturic Acid Formation," *J. Biol. Chem.* 249(22):7130-7139, The American Society for Biological Chemists, Inc., United States (1974).

Harris, J.O., et al., "Serial Gadolinium-enhanced Magnetic Resonance Imaging Scans in Patients with Early, Relapsing-Remitting Multiple Sclerosis: Implications for Clinical Trials and Natural History," *Ann. Neurol.* 29:548-555, American Neurological Association, United States (1991).

Hartung, H.-P., et al., "The Role Of Macrophages And Eicosanoids In The Pathogenesis Of Experimental Allergic Neuritis," *Brain* 111:1039-1059, Oxford University Press, England (1988).

Hemminki, A., et al., "In Vivo Molecular Chemotherapy and Noninvasive Imaging With an Infectivity-Enhanced Adenovirus," *J. Natl. Cancer Inst.* 94(10):741-749, Oxford University Press, United States (2002).

Ji, H., et al., "Different modes of pathogenesis in T-cell-dependent autoimmunity: clues from two TCR transgenic systems," *Immunol. Rev.* 169:139-146, Munksgaard International Publishers, Denmark (1999).

Kappos, L., et al., "Efficacy of a novel oral single-agent Fumarate, BG00012, in patients with relapsing-remitting multiple sclerosis: results of a phase II study," oral presentation on May 30, 2006, at the 16th Meeting of the European Neurological Society, May 27-31, 2006, Lausanne, Switzerland.

Kappos, L., et al., "Efficacy of a novel oral single-agent fumarate, BG00012, in patients with relapsing-remitting multiple sclerosis: results of a phase 2 study," Abstract O108, Proceedings of the 16th Meeting of the European Neurological Society, May 27-31, 2006, Lausanne, Switzerland (Abstract Only).

Kappos, L., et al., "The Efficacy of BG00012 in Patients With Relapsing-Remitting Multiple Sclerosis: Subgroup Analyses From the Phase 2b Study," poster from the 60th Annual Meeting of the American Academy of Neurology, Apr. 12-19, 2008, Chicago, IL, United States.

Kermode, A.G., et al., "Breakdown Of The Blood-Brain Barrier Precedes Symptoms And Other MRI Signs Of New Lesions In Multiple Sclerosis," *Brain* 113:1477-1489, Oxford University Press, England (1990).

"Klinische Studie mit Fumaderm® als magensaftresistente Mikortabletten," Report, (pp. 4-6 are an English language translation of pp. 1-3 of this document).

Kuroda, K., and Akao, M., "Antitumor And Anti-Intoxication Activities Of Fumaric Acid In Cultured Cells," *Gann.* 72(5):777-782, Japanese Cancer Association and the Japanese Foundation for Cancer Research, Japan (1981).

Biosis Database, Accession No. PREV197662032843, English language abstract for Kuroda, K., et al., "Inhibitory Effect Of Capsella-Bursa-Pastoris Extract On Growth Of Ehrlich Solid Tumor In Mice," *Cancer Res.* 36(6):1900-1903, American Assoiciation for Cancer Research, United States (1976) (Abstract Only).

Linker, R.A., et al., "CNTF is a major protective factor in demyelinating CNS disease: A neurotrophic cytokine as modulator in neuroinflammation," *Nature Medicine* 8(6):620-624, Nature America Inc., United States (2002).

Lodie, T.A., et al., "Systematic Analysis of Reportedly Distinct Populations of Multipotent Bone Marrow-Derived Stem Cells Reveals a Lack of Distinction," *Tissue Eng.* 8(5):739-751, Mary Ann Liebert, Inc., United States (2002).

Mendel, I., et al., "A myelin oligodendrocyte glycoprotein peptide induces typical chronic experimental autoimmune encephalomyelitis in H-$2^b$ mice: fine specificity and T cell receptor Vβ expression of encephalitogenic T cells," *Eur. J. Immunol.* 25:1951-1959. VCH Verlagsgesellschaft mbH, Germany (1995).

*The Merck Manual of Diagnosis and Therapy*. 15$^{th}$ Edition, Berkow, R., and Fletcher, A.J., eds., p. 327, Merck Sharp & Dohme Research Lab, United States (1987).

Nieboer, C., et al., "Treatment of psoriasis with fumaric acid derivates," Proceedings of the 239th Meeting of the Netherlands Society for Dermatology and Venereology Amsterdam, Feb. 14, 1987, *Br. J. Dermatol.* 117(6):791-92, Blackwell Scientific Publications, England (1987) (Abstract Only).

(56) References Cited

OTHER PUBLICATIONS

Nioi, P. and Hayes, J.D., "Contribution of NAD(P)H:quinone oxidoreductase 1 to protection against carcinogenesis, and regulation of its gene by the Nrf2 basic-region leucine zipper and the arylhydrocarbon receptor basic helix-loop-helix transcription factors," *Mutat. Res.* 555:149-171, Elsevier B.V., Netherlands (2004).
Olsson, T., "15: Future prospects of cytokines in the pathogenesis and management of multiple sclerosis," in Frontiers in Multiple Sclerosis, vol. 2, p. 139-150, Siva, A., et al., eds., Martin Dunitz Ltd., England (1999).
Olsson, T., "Chapter 6: Cytokines in Multiple Sclerosis and Its Experimental Models," in *Neuroscience Intelligence Unit 5: T-Cell Autoimmunity and Multiple Sclerosis*, Londei, M., ed., p. 91-112, R.G. Landes Company, United States (1999).
Biosis Database, Accession No. PREV199497368291, English language abstract for Pearl, J.M., et al., "Fumarate-enriched blood cardioplegia results in complete functional recovery of immature myocardium," *Ann. Thorac. Surg.* 57(6):1636-1641, Elsevier, Netherlands (1994) (Abstract Only).
Peeters, A.J., et al., "Fumaric Acid Therapy for Psoriatic Arthritis. A Randomized, Double-blind, Placebo-controlled Study," *Br. J. Rheumatol.* XXXI(7):502-504, British Association for Rheumatology and Rehabilitation, England (1992).
Peeters, A.J., et al, "Gunstig effect van fumaarzuurtherapie bij arthritis psoriatica: een dubbelblind, placebo-gecontroleerd onderzoek," *Ned. Tijdschr. Geneeskd.* 136(49):2428-2431, Bohn Stafleu van Loghurn, Netherlands (1992) (Abstract Only in English).
Perrella, O., et al., "Interleukin-10 and IFN-α in multiple sclerosis: is there a balance?" *J. Neurovirol.* 3(Suppl 1):P17, Stockton Press, United States (1997) (Abstract Only).
Polman, C.H., at al., "Diagnostic Criteria for Multiple Sclerosis: 2005 Revisions to the McDonald Criteria," *Ann. Neurol.* 58(6):840-846, Wiley-Liss, Inc., United States (2005).
Prochaska, H.J. and Santamaria, A.B., "Direct Measurement of NAD(P)H:Quinone Reductase from Cells Cultured in Microtiter Wells: A Screening Assay for Anticarcinogenic Enzyme Inducers," *Anal. Biochem.* 169:328-336, Academic Press, Inc., United States (1988).
Roitt, I.M., et al., eds., "23.Autoimmunity and Autoimmune Disease," in *Immunology*, p. 23.1-23.12, Gower Medical Publishing, United States (1985).
Rostami-Yazdi, M., et al., "Detection of Metabolites of Fumaric Acid Esters in Human Urine: Implications for Their Mode of Action," *J. Invest. Dermatol.* 129:231-234, Nature Publishing Group, United States (2008).
Rushmore, T.H., et al., "The Antioxidant Responsive Element: Activation by Oxidative Stress and Identification of the DNA Consensus Sequence Required for Functional Activity," *J. Biol. Chem.* 266(18):11632-11639, The American Society for Biochemistry and Molecular Biology, Inc., United States (1991).
Biosis Database, Accession No. PREV199699044855, English language abstract for Schmidt, K.N, et al., "Anti-psoriatic drug anthralin activates transcription factor NF-kappa-B in murine keratinocytes," *J. Immunol.* 156(11):4514-4519, American Association of Immunologists, United States (1996) (Abstract Only).
Shi, N., et al., "Brain-specific expression of an exogenous gene after i.v. administration," *Proc. Natl. Acad. Sci. USA* 98(22):12754-12759, National Academy of Sciences, United States (2001).
Sobel, R.A., et al. "The Immunopathology Of Experimental Allergic Encephalomyelitis. I. Quantitative Analysis of Inflammatory Cells In Situ," *J. Immunol.* 132(5):2393-2401, American Association of Immunologists, United States (1984).
Stangel, M., et al., "Fumarat in der Behandlung der Multiplen Sklerose: Mögliche Wirkmechanismen und Studien," *Der Nervenarzt* 79:212-217, Springer Medizin Verlag, Germany (2008) (Abstract Only in English).
Stühlinger, W., et al., "Nephrotoxische Wirkung einer Therapie mit Fumarsäureestern bei Psoriasis," *Dtsch. Med. Wschr.* 115:1712-1715, Georg Thieme Verlag Stuttgart, Germany (1990) (Abstract Only in English).

Traugott, U., "Detailed Analysis of Early Immunopathologic Events during Lesion Formation in Acute Experimental Autoimmune Encephalomyelitis," *Cell. Immunol.* 119:114-129, Academic Press, Inc., United States (1989).
Tung, C.-H., et al., "In Vivo Imaging of Proteolytic Enzyme Activity Using a Novel Molecular Reporter," *Cancer Res.* 60:4953-4958, American Association for Cancer Research, Inc., United States (2000).
Tuohy, V.K., et al., "A Synthetic Peptide From Myelin Protelipid Protein Induces Experimental Allergic Encephalomyelitis," *J. Immunol.* 141(4):1126-1130, The American Association of Immunologists, United States (1988).
Üner, A.H., et al., "Characteristics of Auto Anti-idiotypic Antibodies Reactive with Antibodies Expressing the Pathogenic Idiotype, $Id^{LN}F_1$, in the (NZB x SWR)$F_1$ Model for Lupus Nephritis and its Parental Strains," *J. Autoimmun.* 11:233-240, Academic Press, England (1998).
Van Muiswinkel, F.L., et al., "Expression of NAD(P)H:quinone oxidoreductase in normal and Parkinsonian substantia nigra," *Neurobiol. Aging* 25:1253-1262, Elsevier Inc., United States (2004).
Van Muiswinkel, F.L. and Kuiperij, H.B., "The Nrf2-ARE Signalling Pathway: Promising Drug Target to Combat Oxidative Stress in Neurodegenerative Disorders," *Curr. Drug Targets—CNS & Neurol. Disord.* 4:267-281, Bentham Science Publishers Ltd., Netherlands (2005).
Weinmann, I., et al., "Influence Of Fumaric Acid Derivates On T Lymphocytes In The Murine Model Of HSV-1 Keratitis," *Invest. Opthalmol. Vis. Sci.* 41(4):S146, Association for Research in Vision and Ophthalmology annual meeting. Fort Lauderdale, Florida, USA, Apr. 30-May 5, 2000, United States (2000) (Abstract Only).
*The Merck index: An Encyclopedia of Chemicals, Drugs, and Biologicals*, $10^{th}$ Edition, p. 396, Windholz, M., et al., eds., Merck & Co., Inc., United States (1983).
Zamvil, S., et al., "T-cell clones specific for myelin basic protein induce chronic relapsing paralysis and demyelination" *Nature* 317:355-358, Nature Publishing Group, England (1985).
Zamvil, S.S. and Steinman, L., "The T Lymphocyte In Experimental Allergic Encephalomyelitis," *Ann. Rev. Immunol.* 8:579-621, Annual Reviews Inc., United States (1990).
Office Action mailed Dec. 7, 2001, in U.S. Appl. No. 09/831,620, Joshi, R.K., et al., § 371(c) date May 10, 2001 (now U.S. Pat. No. 6,509,376 B1).
Office Action mailed Nov. 28, 2005, in U.S. Appl. No. 10/197,077, Joshi, R.K., et al., filed Jul. 17, 2002 (now U.S. Patent No. 7,320,999 B2).
Office Action mailed Jun. 21, 2006, in U.S. Appl. No. 10/197,077, Joshi, R.K., et al., filed Jul. 17, 2002 (now U.S. Patent No. 7,320,999 B2).
English language Abstract of Chinese Patent Publication No. CN 1125141 A, published Jun. 26, 1996, European Patent Office, Espacenet database—Worldwide (Abstract Only).
Memorandum of Meeting Minutes for the meeting held on Aug. 30, 2006, between attendees from the FDA and Biogen Idec regarding the End of Phase 2 for application PIND 73,061, BG00012.
Altmeyer, P. and Nüchel, C., "Systemtherapie der Psoriasis," *Dtsch. med. Wschr.* 121:1605-1607, Georg Thieme Verlag, Germany (1996).
English language translation of Altmeyer, P. and Nüchel, C., "Systemtherapie der Psoriasis," *Dtsch. med. Wschr.* 121:1605-1607, Georg Thieme Verlag, Germany (1996).
Altmeyer, P. and Nüchel, C., "Systemische Therapie der Psoriasis," *T&E Dermatologie* 27:380-382, 384, Reed Elsevier Deutschland, Germany (1997).
English language translation of Altmeyer, P. and Nüchel, C., "Systemische Therapie der Psoriasis," *T&E Dermatologie* 27:380-382, 384, Reed Elsevier Deutschland, Germany (1997).
Compston, A., et al., "The person with multiple sclerosis: a prospectus," in *McAlpine's Multiple Sclerosis, 4th Edition*, p. 803-810, Compston, A., et al., eds., Elsevier Inc., China (2006).
Kraft, A.D., et al., "Nuclear Factor E2-Related Factor 2-Dependent Antioxidant Response Element Activation by tert-Butylhydroquinone and Sulforaphane Occurring Preferentially in

(56) References Cited

OTHER PUBLICATIONS

Astrocytes Conditions Neurons against Oxidative Insult," *J. Neurosci.* 24(5):1101-1112, Society for Neuroscience, United States (2004).

Malipiero, U., et al., "Myelin oligodendrocyte glycoprotein-induced autoimmune encephalomyelitis is chronic/relapsing in perforin knockout mice, but monophasic in Fas- and Fas ligand-deficient *lpr* and *gld* mice," *Eur. J. Immunol.* 27(12):3151-3160, Wiley-VCH Verlag. GmbH, Germany (1997).

McDonald, W.I., et al., "Recommended Diagnostic Criteria for Multiple Sclerosis: Guidelines from the International Panel on the Diagnosis of Multiple Sclerosis," *Ann. Neurol.* 50(1):121-127, Wiley-Liss, Inc., United States (2001).

Misgeld, T., "Death of an axon: studying axon loss in development and disease," *Histochem. Cell Biol.* 124:189-196, Springer-Verlag, Germany (2005).

Mrowietz, U., "Nephrotoxische Wirkung durch Fumarsäure," *Der Hautarzt 51*:615, Springer-Verlag, Germany (2000).

English language translation of Mrowietz, U., "Nephrotoxische Wirkung durch Fumarsäure," *Der Hautarzt 51*:615, Springer-Verlag, Germany (2000).

Noseworthy, J., et al., "The treatment of symptoms in multiple sclerosis and the role of rehabilitation," in *McAlpine's Multiple Sclerosis, 4th Edition,* p. 701-728, Compston, A., et al., eds., Elsevier Inc., China (2006).

Noseworthy, J., et al., "Disease-modifying treatments in multiple sclerosis," in *McAlpine's Multiple Sclerosis, 4th Edition*, p. 729-802, Compston, A., et al., eds., Elsevier Inc., China (2006).

Riemekasten, G., et al., "Strong Acceleration of Murine Lupus by Injection of the SmD1$^{83\text{-}119}$ Peptide," *Arthritis & Rheum.* 44(10):2435-2445, Wiley-Liss, Inc., United States (2001).

Sadjak, A., et al., "Nephrotoxische Wirkung von Fumarsäurederivaten," *Dtsch. med. Wschr.* 116(12):478, Georg Thieme Verlag, Germany (1991).

English language translation of Sadjak, A., et al., "Nephrotoxische Wirkung von Fumarsäurederivaten," *Dtsch. med. Wschr.* 116(12):478, Georg Thieme Verlag, Germany (1991).

Balasubramaniam, P., et al., "Fumaric acid esters in severe psoriasis, including experience of use in combination with other systemic modalities," *Br. J. Dermatol. 150*:741-746, British Association of Dermatologists, England (2004).

Ffrench-Constant, C., "Pathogenesis of multiple sclerosis," *Lancet* 343(8892):271-275, The Lancet Ltd., England (1994).

Ghoreschi, K., et al., "A molecule solves psoriasis? Systemic therapies for psoriasis inducing interleukin 4 and Th2 responses," *J. Mol. Med. (Berl.)* 81(8):471-480, Springer-Verlag, Germany (2003).

Hartung, H.-P., et al., "Circulating adhesion molecules and inflammatory mediators in demyelination: A review," *Neurology* 45(6)(Suppl. 6):S22-S32, Advanstar Communications Inc., United States (1995).

Lee, J.-M., et al., "Nrf2, a multi-organ protector?" *FASEB J.* 19(9):1061-1066, Federation of American Societies for Experimental Biology, United States (2005).

Loewe, R., et al., "Dimethylfumarate Inhibits Tumor-Necrosis-Factor-Induced CD62E Expression in an NF-κB-Dependent Manner," *J. Invest. Dermatol. 117*:1363-1368, The Society for Investigative Dermatology, United States (2001).

Sormani, M.P., et al., "Clinical trials of multiple sclerosis monitored with enhanced MRI: new sample size calculations based on large data sets," *J. Neurol. Neurosurg. Psychiatry 70*:494-499, British Medical Association, England (2001).

Traugott, U., et al., "Multiple Sclerosis Distribution of T Cells, T Cell Subsets and Ia-positive Macrophages in Lesions of Different Ages," *J. Neuroimmunol. 4*:201-221, Elsevier Science Publishers, Netherlands (1983).

Traugott, U. and Lebon, P., "Multiple Sclerosis: Involvement of Interferons in Lesion Pathogenesis," *Ann. Neurol.* 24(2):243-251, American Neurological Association, United States (1988).

Walsh, M.J. and Tourtellotte, W.W., "Temporal Invariance and Clonal Uniformity Of Brain And Cerebrospinal IgG, IgA, And IgM in Multiple Sclerosis," *J. Exp. Med. 163*:41-53, Rockefeller University Press, United States (1986).

"BG 12 BG 00012, BG 12/Oral Fumarate, FAG-201, Second-Generation Fumarate Derivative—Fumapharm/Biogen Idec," *Drugs in R&D* 6(4):229-230, Adis Data Information BV, New Zealand (2005).

"Efficacy and Safety of BG00012 in MS," ClinicalTrials.gov, accessed at http://www.clinicaltrials.gov/ct2/show/NCT00168701?term=bg00012&rank=3, accessed on Sep. 19, 2008, 3 pages.

"Efficacy and Safety of Oral BG00012 in Relapsing-Remitting Multpile Sclerosis (DEFINE)," ClinicalTrials.gov, accessed at http://www.clinicaltrials.gov/ct2/show/NCT00420212?term=bg00012&rank=1, accessed on Sep. 19, 2008, 4 pages.

"Biogen Idec Announces Positive Top-Line Results from Second Phase 3 Trial Investigating Oral BG-12 (Dimethyl Fumarate) in Multiple Sclerosis," accessed at http://www.biogenidec.com.PRESS_RELEASE_DETAILS.aspx?ID=5981&ReqId=1621631, accessed on Oct. 28, 2011, 3 pages.

Langner, A., et al., "Results of a Phase II Study of a Novel Oral Fumarate BG00012, in the Treatment of Severe Psoriasis," European Congress on Psoriasis, Oct. 21-24, 2004, Paris, France.

Langner, A., et al., "The Efficacy and Safety of a Novel Oral Formulation of Dimethylfumarate, BG00012, in Patients with Severe Psoriasis: Results of a Phase 2 Dose-Finding and Safety Extension Study," 3rd Spring Symposium of the European Academy of Dermatology and Venerology (EADV), 2005, Sofia, Bulgaria.

Langner, A., et al., "Oral Fumarate for the Treatment of Severe Forms of Psoriasis: Results of a Phase II Clinical Study," $2^{nd}$ Spring Symposium of the European Academy of Dermatology and Venerology (EADV) Apr. 29-May 1, 2004, Budapest, Hungary.

Langner, A., et al., "Effects of a Novel Oral Fumarate, BG00012, in Patients with Severe Psoriasis: Results of a Phase 2 Study," $13^{th}$ Congress of the European Academy of Dermatology and Venerology (EADV), Nov. 17-21, 2004, Florence, Italy.

Langner, A., et al., "Efficacy and Safety of a New Oral Formulation of Fumaric Acid Ester for the Treatment of Moderate to Severe Psoriasis," $10^{th}$ International Psoriasis Symposium, Jun. 10-13, 2004, Toronto, Canada.

'T Hart et al., "Modelling of multiple sclerosis: lessons learned in a non-human primate," *The Lancet Neurology* 3(10):588-597, Elsevier Ltd. (2004).

Office Action mailed Jul. 13, 2011, in U.S. Appl. No. 12/526,296, Lukashev et al., § 371(c) Date: Jan. 13, 2011.

Office Action mailed Dec. 15, 2011, in U.S. Appl. No. 12/526,296, Lukashev et al., § 371(c) Date: Jan. 13, 2011.

"Efficacy and Safety Study of Oral BG00012 with Active Reference in Relapsing-Remitting Multiple Sclerosis (CONFIRM)," ClinicalTrials.gov, accessed at http://www.clinicaltrials.gov/ct2/show/NCT00451451?term=bg000 12&rank=8, first received on Mar. 21, 2007, 4 pages.

Office Action mailed Mar. 20, 2012, in U.S. Appl. No. 12/525,805, Gold, § 371(c) Date: Feb. 1, 2010.

International Search Report for International Patent Application No. PCT/US10/01282, International Searching Authority, United States, mailed on Jun. 28, 2010.

International Preliminary Report on Patentability for International Patent Application No. PCT/US10/01282, International Bureau of WIPO, Switzerland, issued Nov. 1, 2011.

Lee, D-H, et al. "Spotlight on fumarates," *Int. MS J.* 15(1):12-18, Cambridge Medical Publications, England (2008).

European Patent Office Communication dated Oct. 30, 2012 in European Patent Application No. EP 08725256.5 regarding observations by a third party.

Schimrigk, S., et al., "Oral fumaric acid esters for the treatment of active multiple sclerosis: an open-label, baseline-controlled pilot study," *European Journal of Neurology* 13(6):604-610, Blackwell Science BV, England, (2006), XP-002496537.

Wienrinckx, A., et al., "Detoxification enzyme inducers modify cytokine production in rat mixed glial cells," *Journal of Neuroimmunnology* 166(1-2):132-143, Elsevier Science Publishers, Netherlands (2005), XP-005000427.

(56) References Cited

OTHER PUBLICATIONS

U.S. Appl. No. 13/955,580, filed Jul. 31, 2013 (Abandoned).
U.S. Appl. No. 13/957,063, filed Aug. 1, 2013 (Abandoned).
U.S. Appl. No. 13/957,117, filed Aug. 1, 2013.
U.S. Appl. No. 13/957,250, filed Aug. 1, 2013.
U.S. Appl. No. 13/957,295, filed Aug. 1, 2013 (Abandoned).
Comi, G., "Disease-modifying treatments for progressive multiple sclerosis," *Multiple Sclerosis Journal* 19(11):1428-1436, SAGE Publications, England (2013).
Ellrichmann, G., et al., "Efficacy of Fumaric Acid Esters in the R6/2 and YAC128 Models of Huntington's Disease," *PLoS One* 6(1):e16172, Public Library of Science, United States (2011).
Bellier, B., et al., "Replacement of glycine with dicarbonyl and related moieties in analogues of the C-terminal pentapeptide of cholecystokinin: $CCK_2$ agonists displaying a novel binding mode," *J. Med. Chem.* 43(20):3614-3623, American Chemical Society, United States (2000).
Choo, H-Y. P., et al., "Design and synthesis of α,β-unsaturated carbonyl compounds as potential ACE inhibitors," *Eur. J. Med. Chem.* 35(6):643-648, Editions Scientifiques Elsevier, France (2000).
Holroyd, S.E., et al., "Rational Design and Binding of Modified Cell-Wall Peptides to Vancomycin-Group Antibiotics: Factorising Free Energy Contributions to Binding", *Tetrahedron* 49(41): 9171-9182, Pergamin Press Ltd., Great Britain (1993).
Kamiyama, T., et al., "Ro 09-1679, a novel thrombin inhibitor," *J. Antibiotics* 45(3):424-427, Japan Antibiotics Research Assn, Japan (1992).
Krstenansky, J.L., et al., "Development of MDL 28,050, a small stable antithrombin agent based on a functional domain of the leech protein, hirudin," *Thrombosis and Haemostasis* 63(2):208-214, Schattauer, Germany (1990).
Bista, P., et al., "Dimethyl Fumarate Suppresses Inflammation In Vitro via Both Nrf2-Dependent and Nrf2-Independent Pathways," poster from the 64th Annual Meeting of the American Academy of Neurology, Apr. 21-28, 2012, New Orleans, LA, USA.
Kappos, L., et al., "BG00012, a novel oral fumarate, is effective in patients with relapsing-remitting multiple sclerosis," *Multiple Sclerosis* 12(1):S85, Sage Publications, England (2006).
Lukashev Matvey et al., "Activation of Nrf2 and modulation of disease by BG00012 (dimethyl fumarate) suggest a dual cytoprotective and anti-inflammatory mechanism," *Neurology* 70(11):A27, 60th Annual Meeting of the American Academy of Neurology, Apr. 12-19, United States (2008)
Ryan Sarah et al., "Dimethyl Fumarate (BG00012) Inhibits Astrogliosis in Rodent EAE Models," *Neurology* 72(11), 61st Annual Meeting of Ameircan Academy of Neurology, Apr. 28-29, United States (2009).
Office Action mailed Feb. 14, 2013, in U.S. Appl. No. 13/266,997, inventor Matvey Lukashev, §371 (c) date: Jan. 12, 2012.
Office Action mailed Oct. 7, 2013, in U.S. Appl. No. 13/760,916, inventors Golman et al., filed Feb. 6, 2013.
Gold, R., et al., "Safety of a novel oral single-agent fumarate, BG00012, in patients with relapsing-remitting multiple sclerosis: results of a phase 2 study," Sixteenth Meeting of the European Neurological Society, *J Neurol* 253 (Suppl 2): II/144-II/145, Springer Verlag, Germany (May 2006).
Choi, H. J., et al., "Tetrahydrobiopterin causes mitochondrial dysfunction in dopamingergic cells: Implications for Parkinson's disease," *Neurochem. Int.* 48(4):255-262, Pergamon Press, England (2006).
Vaknin, I., et al., "Excess Circulating alternatively activates myeloid (M2) cells accelerate ALS progression while inhibiting experimental autoimmune encephalomyelitis," *PLoS ONE* 6(11):e26291, Public Library of Science, United States (2011).
U.S. Appl. No. 14/136,990, inventor Jianhua Chao, filed Dec. 20, 2013 (Not Published).
Office Action mailed Dec. 19, 2013, in U.S. Appl. No. 12/525,805, inventor Ralf Gold, filed Feb. 1, 2010.
Office Action mailed Oct. 29, 2013, in U.S. Appl. No. 13/826,354, inventor Ralf Gold, filed Mar. 14, 2013.
Van Walderveen, M.A., et al., "Development of hypointense lesions on T1-weighted spin-echo magnetic resonance images in multiple sclerosis: relation to inflammatory acctivity," *Arch. Neurol.* 56(3):345-351, American Medical Assn., United States (1999).
Borel, J.F., et al., "Biological Effects of Cyclosporin A: A new Antilymphocytic Agent," *Agents and Actions* 6(4):468-475, Birkhäuser Verlag, Switzerland (1976).
Borel, J.F., et al., "Effects of the new anti-lymphocytic peptide cyclosporin A in animals," *Immunology* 32:1017-1025, British Society for Immunology, England (1977).
De Haan, P. and Lerk, C.F., "Oral controlled release dosage forms. A review," *Pharmaceutish Weekblad Scientific Edition* 6:57-67, Utrecht, Bohn, Scheltema & Holkema, the Netherlands (1984).
Tracy Staton, "A prosperous new year for pharma? Let's check the tea leaves," fiercepharma.com, accessed at http://www.fiercepharma.com/node/119361/print, accessed on Jan. 3, 2014, 3 pages.
Biogen Idec: Investors: Press Release, "Biogen Idec Announces Positive Top-Line Results from the First Phase 3 Trial Investigating Oral Bg-12 (Dimethyl Fumarate) in Multiple Sclerosis," published on Apr. 11, 2011, 2 pages.
Biogen Idec: Investors: Press Release, "Biogen Idec Announces Positive Top-Line Results from Second Phase 3 Trial Investigating Oral Bg-12 (Dimethyl Fumarate) in Multiple Sclerosis," published on Oct. 26, 2011, 2 pages.
Meg Tirrell, "Biogen MS Pill With $3 Billion Potential Hits Study Goals," bloomberg.com, accessed at http://www.bloomberg.com/news/2011-20-26/biogen-multiple-sclerosis-pill-bg-12-cuts-relapses-in-late-stage-study.html, accessed on Jul. 10, 2012, 4 pages.
Christopher Comfort, "For the Treatment of Multiple Sclerosis, More Than 85 Percent of Surveyed Neurologists in the EU5 Expect to Prescribe Biogen Idec's BG-12, Sanofi/Genzyme's Aubagio and Sanofi/Genyzme/Bayer HealthCare's Lemtrada," Decision Resources LLC, accessed at http://decisionresources.com/News-and-Events/Press-Releases/Multiple-Sclerosis-062512, accessed on Jul. 10, 2012, 2 pages.
Galeone, M., et al., "In Vivo Demonstration of Delivery Mechanisms From Sustained-Release Pellets," *Current Therapeutic Research* 29(1):217-234, Therapeutic Research Press, Inc., United States (1981).
Howard, M., et al., "Biological Properties of Interleukin 10," *Journal of Clinical Immunology* 12(4):239-247, Plenum Publishing Company, United States (1992).
Kunst, L., et al., "Fumaarzuurtherapie bij Psoriasis" *TIG* Jun. 14, 1998:243-251, the Netherlands (1998).
Certified English translation of Kunst, L., et al., "Fumaarzuurtherapie bij Psoriasis" *TIG* Jun. 14, 1998:243-251, the Netherlands (1998) by Park IP Transations.
Mrowietz, U., et al., "Treatment of severe psoriasis with fumaric acid esters: scientific background and guidelines for therapeutic use," *British Journal of Dermatology* 141:424-429, British Association of Dermatologists, England (1999).
Shaw, L.M., "Advances in Cyclosporine Pharmacology, Measurement and Therapeutic Monitoring," *Clin. Chem.* 35(7):1299-1308, The American Association for Clinical Chemistry, United States (1989).
Stähelin, H.F., "The history of cyclosporin A (Sandimmune®) revisited: Another point of view," *Experientia* 52:5-113, Birkhäuser Verlag, Switzerland (1996).
Summary of Product Characteristics/SPC, Fumaderm® initial/Fumaderm® (Translation of the original German version) (2006).
Tabandeh, H., et al., "Preparation of Sustained-Release Matrix Tablets of Aspirin with Ethylcellulose, Eudragit RS100 and Eudragit S100 and Studying the Release Profiles and their Sensitivity to Tablet Hardness," *Iranian Journal of Pharmaceutical Research* 2:201-206, School of Pharmacy, Shaheed Beheshti University of Medical Sciences, Iran (2003).
*Fiedler Encyclopedia of Excipients for Pharmaceuticals, Cosmetics, and Related Areas*, Sixth Edition, Hoepfner, E.-M., et al., eds., pp. 580 and 603-605, Editio Cantor Verlag Aulendorf, Germany (2007).

(56) References Cited

OTHER PUBLICATIONS

Handbook of Pharmaceutical Excipients, Hydroxypropyl Cellulose, p. 289, Pharmaceutical Press and American Pharmaceutical Association, London, UK (2003).
Upadrashta, S.M., et al., "Direct Compression Controlled Release Tablets Using Ethylcellulose matrices," *Drug Development and Industrial Pharmacy* 19(4):449-460, Marcel Dekker, Inc, United States (1993).
Hogan, J., "Coating of tablets and multiparticulates," in *Pharmaceutics: The Science of Dosage Form Design*, Second Edition, Aulton, M.F., ed., pp. 441-448, Churchill Livingstone, Elsevier Limited, Edinburgh, United Kingdom (2002).
Office Action mailed Nov. 22, 2013, in U.S. Appl. No. 13/804,283, inventor Matvey E. Lukashec, filed Mar. 14, 2013.
Sczesny-Kaiser M et al. "Synergismus von Interferon [beta]-1 b und Fumasaure?", *Aktuelle Neurologie*, 36(3):S284-S286, Thieme Stutigart, DE (2009).
U.S. Appl. No. 13/578,430, inventors Goelz et al., international filing date Feb. 11, 2011.
U.S. Appl. No. 13/800,128, inventors Joshi et al., filed Mar. 13, 2013.
Office Action mailed Apr. 26, 2013, in U.S. Appl. No. 13/040,914, Joshi et al., filed Mar. 4, 2011.
Notice of Allowance mailed Oct. 24, 2013, in U.S. Appl. No. 13/040,914, Joshi et al., filed Mar. 4, 2011.
Office Action mailed Aug. 28, 2012, in U.S. Appl. No. 13/465,740, inventor Lukashev, M.E., filed May 7, 2012.
Mier, J. and Segura, C. of Nafar Laboratories, S.A. DE C.V., Initial Submission to the General Director of the Mexican Institute of Industrial Property, "Solitud de declaración administrative de nulidad de la Patente 221370 'USO DE Dialquifumaratos'," dated Oct. 4, 2013, filed Oct. 9, 2013, a copy as recieved from Clarke, Modet & C° México.
Mier, J. and Segura, C. of Nafar Laboratories, S.A. DE C.V., Initial Submission to the General Director of the Mexican Institute of Industrial Property, "Application for the Administrative Declaration of Invalidity of Patent No. 221370 'Utilization of Dialkyl Fumarates'," dated Oct. 4, 2013, filed Oct. 9, 2013.
Juárez, M. A. P. of Clarke, Modet & C° México representing Fumapharm AG., Original Spanish Submission to the General Director of the Mexican Institute of the Industrial Property in response to the Initial Submission by Nafar Laboratorios, S.A. de C.V., dated Jan. 7, 2014.
English language summary of substantive arguments made in the original Spanish submission dated Jan. 7, 2014.
Arastoo, A.A., et al., "The comparison of effect of 8 weeks aerobic and yoga training on physiological cost index in multiple sclerosis," *Sci Med J* 10(2):153-162, Iran (2011).
Biogen Idec, "2007 Research & Development Day," 27 slides, Boston, MA, USA, May 17, 2007.
Biogen Idec, "Biogen Idec Announces May 17 Webcast of Research & Development Day," BusinessWire, 1 page, Cambridge, MA, USA, May 11, 2007.
Biogen Idec Press Release, "US and EU Regulatory Authorities Accept Oral BG-12 Marketing Applications for Review," Business Wire, Weston, MA, May 9, 2012.
Ema, "Questions and answers on the ongoing review of Gilenya (fingolimod)," *European Medicines Agency*, EMA/43541/2012, EMEA/H/C/000539, Jan. 19, 2012, 2 pages.
Emea, ICH Topic E4: Dose Response Information to Support Drug Registration, *Step 5, Note for Guidance on Dose Response Information to Support Drug Registration*, UK, Nov. 1994.
Fox, R., et al., "Phase 3 Clinical Program to Assess Efficacy and Safety of BG00012 in MS," *Abstracts from the 21$^{st}$ Annual Meeting of the Consortium of Multiple Sclerosis Centers: The Challenges of Care and Research in Multiple Sclerosis* (S34), Washington, D.C. May 30-Jun 2, 2007.
Gold, R., et al., "Two phase 3 studies to determine the efficacy and safety of BG00012, a novel, oral fumaric acid derivative, in patients with relapsing multiple sclerosis," *23$^{rd}$ ECTRIMS conference and 12th RIMS Conference: Immunomodulation 2*, Oct. 13, 2007.
Gold, R, "Oral Therapies for Multiple Sclerosis: A Review of Agents in Phase III Developments or Recently Approved," *CNS Drugs* 25(1):37-52, Adis International, New Zealand (2011).
Killestein, J., el al., "Oral treatment for multiple sclerosis," *The Lancet Neurology* 10(1):1026-1034 (2011).
National Multiple Sclerosis Society, "Clinical Trials in Multiple Sclerosis 2007: Planned, In Progress, Recently Completed," National Multiple Sclerosis Society, Research & Clinical Programs, USA (2007).
Sheridan C., "Safety profiles come to fore as more drugs approach MS market," *Nature Biotechnology* 30(1):6-8, Nature America Publishing, USA (2012).
"Trial Watch: Phase III success for Biogen's oral multiple sclerosis therapy," *Nature Review Drug Discovery 10*:404, Nature Publishing Group, England (2011).
U.S. Department of Health & Human Services, "Exposure-Response Relationships—Study Design, Data Analysis, and Regulatory Applications," *Guidance for Industry*, U.S. Department of Health & Human Services, pp. 1-23, USA, Apr. 2003.
U.S Food and Drug Administration, "FDA News Release : FDA Approves first oral drug to reduce MS relapses," U.S. Department of Health & Human Services, 1 page, USA, Sep. 22, 2010.
Fox, R., "BG00012—A Novel Oral Therapy in Development for the Treatment of Multiple Sclerosis," US Neurological Disease 2007(2): 32-36, USA (2007).

\* cited by examiner

USE OF FUMARIC ACID DERIVATIVES FOR TREATING CARDIAC INSUFFICIENCY, AND ASTHMA

This application is a continuation of application Ser. No. 10/571,241, which is a National Stage of International Application No. PCT/EP04/009835, filed Sep. 3, 2004, which claims the benefits of German Application No. 103 41 530.0, filed Sep. 9, 2003, and German Application No. 103 60 869.9, filed Dec. 23, 2003, all of which are incorporated herein by reference.

The present invention relates to the use of fumaric acid derivatives for preparing a drug for treating cardiac insufficiency, and asthma.

PRIOR ART

Fumaric acid dialkyl esters and fumaric acid monoalkyl esters and salts thereof have been successfully used for treating psoriasis for a long time. The use has been described in a number of patents, cf. e.g. DE 25 30 372, DE 26 21 214 or EP-B-0 312 697.

Also, the use of fumaric acid mono- and diesters for treating autoimmune diseases such as e.g. polyarthritis or multiple sclerosis (cf. DE 197 21 099.6 and DE 198 53 487.6), but also for use in transplantation medicine (cf. DE 198 53 487.6 and DE 198 39 566.3) has been described. Moreover, the use of fumaric acid mono- and diesters for treating NFkappaB-mediated diseases as well as the treatment of mitochondrial diseases and/or as NFkappaB inhibitor is known from DE 101 01 307.8 and DE 100 00 577.2. All mentioned publications describe fumaric acid mono- and diesters, optionally in the form of certain salts.

Also, the use of fumaric acid mono- and diamides for treating said indications is known from DE 101 33 004.9. These amides are formed with amino acids and preferably with specific peptides. Finally, fumaric acid oligomers and their use for treating said diseases are known from DE 102 17 314.1.

A paroxysmal, marked respiratory distress is understood by asthma (bronchial asthma) from which approx. 4 to 5% of the population of the industrial nations are suffering, there being an upward tendency. This respiratory distress is based on a variable and reversible obstruction of the respiratory tract due to a hyperreactive bronchial system, which is triggered by exogenic and/or endogenic stimuli. These include chemical or physical provocative factors, infections, physical effort and/or emotional factors. After a longer duration of the disease, secondary diseases such as a chronic bronchitis, a pulmonary emphysema, bronchiectases, atelectases or a pulmonary heart disease or a respiratory cardiac insufficiency usually occur.

Depending upon the cause, differentiation is made between the following variants of asthma, namely asthma caused by allergies, infections, analgesics, job conditions or physical effort, mixed forms of asthma or asthma cardiale (cardiac asthma), nasal asthma and asthma uremicum. In particular, asthma cardiale may result in respiratory distress due to increased congestion in the lesser circulation in the case of a left ventricular insufficiency.

Nowadays, beta-2 sympathomimetics, corticosteroids, parasympatholytics, theophylline, anti-inflammatory agents and anti-allergic agents are, for instance, administered in the drug treatment of and/or for alleviating asthma, in addition to the still proven means of just avoiding the triggering stimulus.

On a molecular level, asthma seems to be characterized by an increased activity of Th2 lymphocytes in the lung, which, in turn, results in an increased release of some Th2 cytokines which, ultimately, gives rise to the known features of asthma such as IgE isotype switching, mucus production and recruitment and activation of eosinophils. Moreover, Th2 cytokines seem to result in the differentiation of further Th2 cells through the signal transduction pathway known as JAK-STAT, from which a self-enhancing circle results. An increased proliferation of mesenchymal cells, in particular bronchial smooth muscle cells, was also observed.

The so-called JAK-STAT signal transduction pathway (JAnus Kinase Signal Transducer and Activator of Transcription pathway) is a pathway for transmitting information to be transmitted by signal peptides such as e.g. cytokines to the interior of the cell and/or the nucleus. Signal transduction takes place through STAT proteins that are present in the cytoplasm and are at first inactive; 7 different STAT proteins are know in man. As a result of a receptor ligand bonding on the cell surface, these STAT proteins are quickly activated by means of phosphorylation, e.g. by means of the Janus kinase. Phosphorylation results in the homo- or heterodimerization of the STAT proteins, the dimers being rapidly trans-ported into the nucleus, where they bond to a target promoter and drastically enhance the transcription rate of this promoter.

An acute or chronic inability of the heart to deliver the output of blood required for metabolism and/or receive the venous return under stress (stress insufficiency) or already at rest (=rest insufficiency) are understood by cardiac insufficiency. The insufficiency may occur as a pure left ventricular or right ventricular insufficiency, but may as well affect both ventricles.

The clinical picture of cardiac insufficiency can be attributed to various causes in terms of etiology, above all to inflammatory and degenerative changes of the myocardium and endocardium, coronary circulatory disorders, myocardial infarction and injuries. Subsequently, cardiac insufficiency results in changes in the peripheral circulation, breathing disorders, in particular cardiac asthma, renal insufficiency and disorders of the electrolyte metabolism and edemas and a reduced functional capacity of the skeletal muscles.

As regards to the indication, differentiation is made between acute cardiac insufficiency, energetic cardiac insufficiency, energetic-dynamic cardiac insufficiency and hypodynamic cardiac insufficiency, also called HEGGLIN syndrome II, excitomotoric cardiac insufficiency, cardiac insufficiency as a result of cardiac arrythmics, hypoxemic, latent, primary, compensated, relative or stress insufficiency and/or left ventricular insufficiency.

At present, contraction-promoting substances are used for the drug treatment of cardiac insufficiency, glycosides (above all digoxin and digitoxin) being still used today for treating the chronic forms. However, during the last few years, vasodilators (nitro-compounds and dihydralazine, alpha blockers, calcium antagonists and above all ACE inhibitors) have gained in importance. ACE inhibitors are most important for long-term treatment. Moreover, diuretics are used. Acute forms are treated with catecholamines, possibly also with amrinone.

It is an object of the invention to provide a further agent for the treatment of cardiac insufficiency and asthma. In particular, it is an object of the invention to provide a therapeutic agent for both cardiac asthma and left ventricular insufficiency in the area in which they overlap with each other. It is another object of the invention to provide a therapeutic agent for both indications individually or in the area in which they overlap with each other, which, due to its good tolerance, is suited for long-term therapy.

The present object is attained by the use of fumaric acid derivatives for preparing pharmaceuticals or pharmaceutical preparations for treating asthma and/or cardiac insufficiency, in particular in man.

SUMMARY OF THE INVENTION

According to a first aspect the invention relates to the use of fumaric acid derivatives selected from the group consisting of dialkyl fumarates, monoalkyl hydrogen fumarates, fumaric acid monoalkyl ester salts, fumaric acid monoamides, monoamido fumaric acid salts, fumaric acid diamides, monoalkyl monoamido fumarates, carbocyclic and oxacarbocyclic oligomers of these compounds and mixtures thereof for preparing a pharmaceutical preparation for the treatment or prevention of cardiac insufficiency, in particular left ventricular insufficiency, myocardial infarction and angina pectoris.

According to a second aspect the invention relates to the use of fumaric acid derivatives, selected from the group consisting of dialkyl fumarates, monoalkyl hydrogen fumarates, fumaric acid monoalkyl ester salts, fumaric acid monoamides, monoamido fumaric acid salts, fumaric acid diamides, monoalkyl monoamido fumarates, carbocyclic and oxacarbocyclic oligomers of these compounds and mixtures thereof for preparing a pharmaceutical preparation for the treatment of asthma and chronic obstructive pulmonary diseases, especially asthma caused by allergies, infections, analgesics, job conditions or physical effort, mixed forms of asthma, or asthma cardiale.

The present invention likewise concerns a method for inhibiting $^3$H-thymidine uptake by bronchial smooth muscle cells, and a method of inhibiting proliferation of these cells as described below and in the appending claims.

The present invention finally concerns the use of the above fumaric acid derivatives for inhibiting the PDGF induced STAT1 activation.

DETAILED DESCRIPTION OF THE INVENTION

Figure 1:
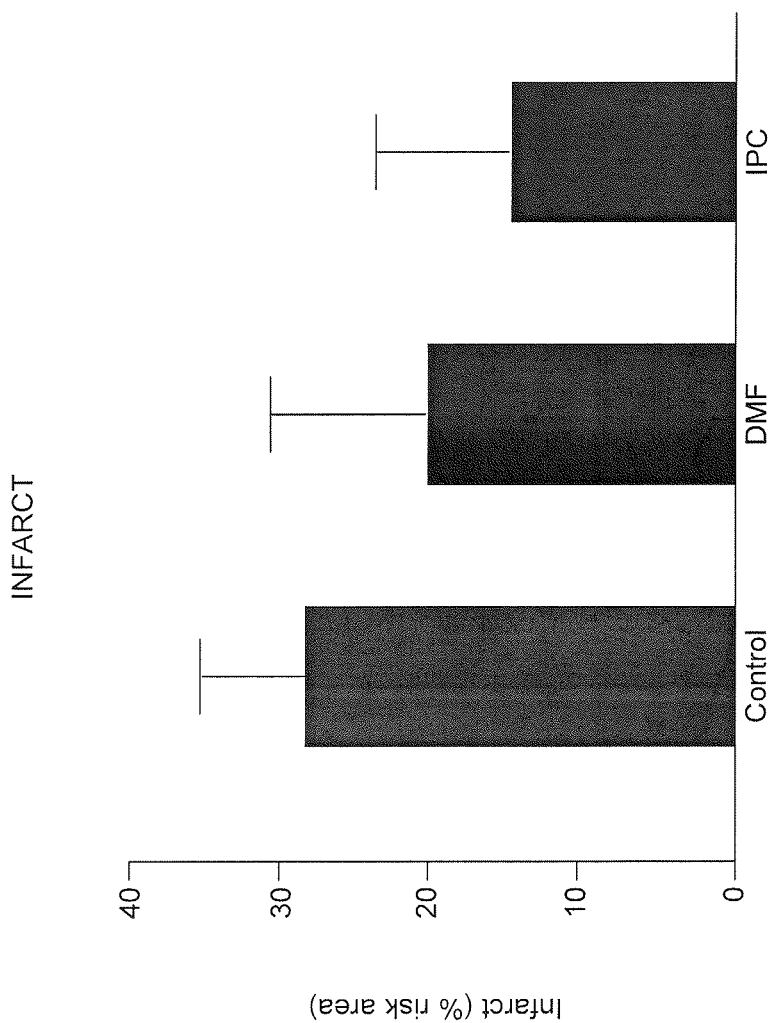
FIG. 1 is a bar chart which shows the extent of infarctions after administration of DMF, ischemia and for controls.

According to one aspect thereof the present invention relates to the use of fumaric acid derivatives for preparing a pharmaceutical preparation for treating asthma and chronic obstructive pulmonary diseases in general. Preferably, this asthma is caused by allergies, infections, analgesics, job conditions or physical effort, particularly preferred asthma cardiale.

According to a second aspect thereof the invention also relates to the use of fumaric acid derivatives for preparing a pharmaceutical preparation for treating or preventing cardiac insufficiency, myocardial infarction and angina pectoris. The cardiac insufficiency concerned may be any type of cardiac insufficiency regardless of its form and/or etiology. Examples of cardiac insufficiency to be treated according to the invention are acute cardiac insufficiency, energetic cardiac insufficiency, energetic-dynamic cardiac insufficiency and hypodynamic cardiac insufficiency, also called HEGGLIN syndrome H, excitomotor cardiac insufficiency, cardiac insufficiency as a result of cardiac irregularities, hypoxemic, latent, primary, compensated, decompensated, relative or stress insufficiency and/or left ventricular insufficiency most preferably, left ventricular insufficiency. The compositions are also effective in preventing these illnesses and/or myocordial infarctions, including first, second or further infarctions.

These uses are based on the finding that fumaric acid derivatives inhibit PDGF—(platelet derived growth factor) induced STAT1 activation. As described above, it was assumed that, in asthma, STAT activation results in a shifting of the cytokine pattern and, ultimately, in a vicious circle with increased Th2 cell activity and the consequences of mucous secretion, IgE production and recruiting of eosinophils (A. B. Pernis, P. B. Rothman, "JAK-STAT signalling in asthma" in: The J. of Clin. Investigation, vol. 10, No. 1, May 2002).

The shifting of the cytokine pattern from Th1 to Th2 that is described in the literature for the substance class of fumaric acid derivatives (cf. the aforementioned patent specifications) would rather give rise to expecting an intensification of this vicious circle. Accordingly, they would not be suited for treating asthma. Surprisingly, it turned out that fumaric acid derivatives can inhibit the proliferation of smooth muscle cells of the respiratory tract. This seems to take place through the inhibition of the PDGF-inducible transcription factor STAT1. It was possible to specifically show that fumaric acid derivatives can inhibit the PDGF-induced STAT1 activation and the PDGF-stimulated thymidine incorporation in BSM (bronchial smooth muscle) cells. Without wanting to be bound thereby, this proliferation-inhibiting effect could be causal for both the effectiveness of fumaric acid derivatives in the therapy of asthma.

The fumaric acid derivatives to be used according to the invention may be one or several selected from the group consisting of dialkyl fumarates (fumaric acid dialkyl esters, respectively), monoalkyl hydrogen fumarates (fumaric acid monoalkyl esters, respectively), monoalkyl ester fumaric acid salts (fumaric acid monoalkyl ester salts, respectively) of physiologically acceptable cations, in particular alkaline or alkaline earth metal cations or transition metal cations such as Li$^+$, Na$^+$, K$^+$, NH$_4^+$, Mg$^{2+}$, Ca$^{2+}$, Fe$^{2+}$, Mn$^{2+}$, and Zn$^{2+}$, fumaric acid monoamides and fumaric acid diamides and their salts, carbocyclic and oxacarbocyclic oligomers of these compounds and mixtures thereof.

In a preferred embodiment the fumaric acid derivative is selected from the group consisting of optionally substituted fumaric acid dialkyl esters and fumaric acid monoalkyl esters in the form of the free acid or its salts and mixtures thereof.

Particularly preferred in this case is the use of fumaric acid dialkyl esters of the formula (I)

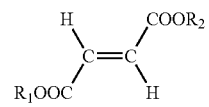

as they are described in DE 198 53 487.6, wherein R$_1$ and R$_2$ which may be the same or different independently represent a C$_{1-24}$ alkyl radical or a C$_{5-20}$ aryl radical and these radicals are optionally substituted with halogen (F, Cl, Br, I), hydroxy, $C_{1-4}$ alkoxy, nitro or cyano. With special preference, the dialkyl fumarate is dimethyl fumarate, diethyl fumarate and/or methyl ethyl fumarate.

In general, an alkyl group is to be understood as a saturated or unsaturated, straight-chain, branched or cyclic hydrocarbon group having 1 to 24 carbon atoms according to the invention, which may be optionally substituted with one or more substituents. Preferably, the alkyl group is methyl, ethyl, n-propyl, isopropyl, n-butyl, sec-butyl, t-butyl, pentyl, cyclopentyl, 2-ethylhexyl, hexyl, cyclohexyl, heptyl, cycloheptyl, octyl, vinyl, allyl, 2-hydroxy ethyl, 2-hydroxy propyl, 3-hydroxy propyl, 2,3-dihydroxypropyl, 2-methoxy ethyl, methoxy methyl, 2-methoxy propyl, 3-methoxy propyl or 2,3-dimethoxy propyl. Methyl or ethyl are most preferred.

According to the invention an aryl group is to be understood as an optionally substituted aryl, alkyl substituted aryl or aralkyl group having 5 to 20 carbon atoms, preferably an aryl, alkyl substituted aryl or aralkyl group having 6 to 10 carbon atoms. Exemplary groups are phenyl, benzyl, phenethyl, methyl phenyl, ethyl phenyl, propyl phenyl and butyl phenyl, t-butyl phenyl, phenyl and benzyl being especially preferred.

The substituents of said groups are preferably selected from the group consisting of halogen (F, Cl, Br, I), hydroxy, $C_{1-4}$ alkoxy, $C_{1-4}$ alkyl, nitro and cyano.

Fumaric acid monoalkyl esters of the formula (II)

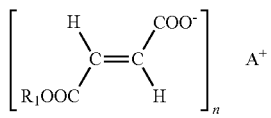

as they are described in DE 197 21 099.6 can also be advantageously used, wherein $R_1$ is as defined above, A is hydrogen, an alkaline or alkaline earth metal cation or a physiologically acceptable transition metal cation, preferably selected from $Li^+$, $Na^+$, $K^+$, $Mg^{2+}$, $Ca^{2+}$, $Zn^{2+}$, $Fe^{2+}$, and $Mn^{2+}$, and n equals 1 or 2 and corresponds to the valence of A.

Exemplary compounds of the formulae (I) and (II) are fumaric acid dimethyl ester, fumaric acid diethyl ester, fumaric acid methyl ethyl ester, methyl hydrogen fumarate, ethyl hydrogen fumarate, calcium methyl fumarate, calcium ethyl fumarate, magnesium methyl fumarate, magnesium ethyl fumarate, zinc methyl fumarate, zinc ethyl fumarate, iron methyl fumarate and iron ethyl fumarate. They can be used individually or as mixtures.

Preferably, the fumaric acid amides to be used according to the invention are those described in DE 101 33 004.9. They correspond to the general formula (III)

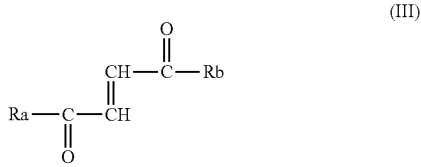

wherein
$R_a$ represents $OR_3$ or a D- or L-amino acid radical —NH—$CHR_4$—COOH bonded via an amide bond, wherein $R_3$ is hydrogen, a straight-chain or branched, optionally substituted $C_{1-24}$ alkyl radical, a phenyl radical or a $C_{6-10}$ aryl or aralkyl radical and $R_4$ is a side chain of a natural or synthetic amino acid; and $R_b$ represents a D- or L-amino acid radical —NH—$CHR_5$—COOH bonded via an amide bond, wherein $R_5$ is a side chain of a natural or synthetic amino acid, or a peptide radical with 2 to 100 amino acids bonded via an amide bond, wherein each amino acid may be the same or different.

The side chain of a natural or synthetic amino acid is typically a side chain selected from the group consisting of the side chains of Ala, Val, Leu, Ile, Trp, Phe, Met, Tyr, Thr, Cys, Asn, Gln, Asp, Glu, Lys, Arg, His, Citrulline, Hcy, Hse, Hyp, Hyl, Orn, Sar, and Me-Gly. The side chains of Gly, Ala, Val, Ile, Leu, and Me-Gly are preferred. If $R_a$ is an L amino acid radical —NH—$CHR_4$—COOH and $R_b$ is an L-amino acid radical —NH—$CHR_5$—COOH, $R_4$ and $R_5$ may be the same or different. More preferably, $R_4$ and $R_5$ are the same. Most preferably $R_a$ and $R_b$ each are glycine.

Alternatively, $R_a$ may be the radical —$OR_3$, and $R_b$ may be an L-amino acid radical —NH—$CHR_5$—COOH or a peptide radical, $R_5$ having the meaning indicated above. In this case, the fumaric acid derivative is a monoalkyl monoamido fumarate.

The peptide radical is bonded via an amide bond and has 2 to 100, preferably 2 to 30, most preferably 2 to 15 amino acids, which may be the same or different. The peptide radical $R_b$ is most preferably selected from the group consisting of peptide hormones, growth factors, cytokines, neurotransmitters, neuropeptides, antibody fragments, coagulation factors and cyclosporines and derivatives and fragments thereof. Preferably, $R_a$ is methoxy or ethoxy and $R_b$ is Gly, Ala, Val, Ile, Leu and Me-Gly.

The fumaric acid amides as defined above can be used individually or in admixture or also in mixture with the fumaric acid monoalkyl or dialkyl esters defined above.

Finally, carbocyclic or oxacarbocyclic fumaric acid oligomers can also be used as they are described in DE 102 17 314.1. They contain 2 to 10, preferably 2 to 6 and most preferably 2 to 3 units derived from fumaric acid and/or its esters and/or amides as defined above as repetitive units.

These fumaric acid oligomers are preferably obtained by means of the (olefinic) polymerization of the C—C double bonds (for the carbocyclic oligomers) and/or the C—C double bonds and the carbonyl oxygens of the units (for the oxacarbocyclic oligomers). Preferably, the units derived from the fumaric acid are derived from monomers selected from the group consisting of fumaric acid and the dialkyl fumarates, monoalkyl hydrogen fumarates, fumaric acid monoamides, fumaric acid diamides, monoalkyl monoamido fumarates and their salts and mixtures thereof, which are defined above. More preferably, the oligomer only contains units derived from one or two monomers. Most preferably, the oligomer exclusively contains identical monomer units.

The carbocyclic oligomers are composed of the units derived from the fumaric acid in such a way that the units are bonded to the carbon atoms 2 and 3 of the fumaric acid backbone by means of covalent C—C bonds in such a way that a carbocyclic oligomer is formed. The oligomer backbone comprises an even number of carbon atoms and does not contain any other monomers and/or heteroatoms. This backbone is substituted at each carbon atom with one of the carboxylic acid and/or carboxylic acid amide groups of the fumaric acid monomer unit(s), from which it is built up.

The oxacarbocyclic oligomers are composed of the fumaric acid monomers in such a way that the units are bonded to each other at the carbon atoms 1 and 3 via ether bridges. At the same time, the ethylenic unsaturation of the atoms $C_2$ and $C_3$ is shifted to $C_1$ and $C_2$. Thus, the ring contains polyoxypropene units in the case of the oxacarbocyclic oligomers according to the invention.

The term "oligomer" used herein relates to a number of at least two fumaric acid monomer units. Customarily, the oxacarbocyclic and/or carbocyclic fumaric acid oligomer contains 2 to 10, preferably 2 to 6 and most preferably 2 to 3 units derived from fumaric acid. Preferably, the carboxylic acid and/or carboxylic acid amide groups as substituents of the cycle are all in a trans-position to each other.

In a preferred embodiment, a carbocyclic fumaric acid oligomer corresponding to the following formula (IVa)

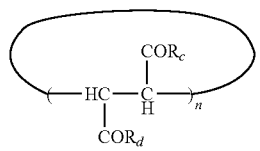

is used, wherein the radicals $R_c$ and $R_d$ are the same or different and are selected among amine radicals (—$NR_1R_2$), amino acid radicals —NH—C(COOH)—$R_5$, peptide radicals having 2 to 100 amino acids, alkoxy radicals (—$OR_1$) and a hydroxyl radical, $R_1$, $R_2$ and $R_5$ being as defined above and n being an integer from 2 to 10 inclusive, preferably 2 to 6 inclusive.

Preferably, the radicals $R_c$ and $R_d$ each are independently an alkoxyl or hydroxyl radical, $R_c$ and $R_d$ not meaning hydroxyl at the same time with the greatest preference. Thus, the monomer(s) is (are) preferably one or several monoalkyl hydrogen fumarate(s). In another embodiment both radicals $R_c$ and $R_d$ may represent an alkoxy radical —$OR_1$ which, still more preferred, is identical. In this case, the monomer(s) is (are) dialkyl fumarates.

Very preferably, the r-1,t-2,c-3,t-4-tetrakis(methoxy carbonyl)cyclobutane or the r-1,t-2,c-3,t-4,c-5,t-6-hexa(alkoxy carbonyl)cyclohexane, preferably the r-1,t-2,c-3,t-4-tetrakis (methoxy carbonyl)cyclobutane and/or the r-1,t-2,c-3,t-4-c-5,t-6-hexa(methoxy carbonyl)cyclohexane is used according to this embodiment.

Alternatively, the oxacarbocylic oligomer of the formula (IVb):

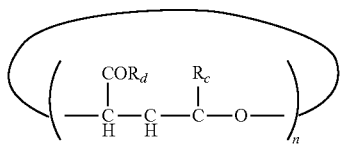

n = 2' to 10 is used, wherein $R_c$ and $R_d$ are as defined above and n is an integer from 2 to 10 inclusive, more preferably 2 to 6 inclusive.

The fumaric acid derivatives to be used according to the invention can be prepared according to known processes as they are e.g. described in DE 197 21 099.6, DE 101 33 004.9 or DE 102 17 314.1. The content of these publications is incorporated herein by reference.

The pharmaceutical preparation may be present in a form suitable for oral, rectal, transdermal, dermal, ophthalmological, nasal, pulmonary or parenteral application. Preferably, the pharmaceutical preparation is suited for oral administration. It may then be present in the form of tablets, coated tablets, capsules, granulate, solutions for drinking, liposomes, nano-particles, nano-capsules, micro-capsules, micro-tablets, pellets or powders and in the form of granulate filled in capsules or sachets, micro-tablets filled in capsules or sachets, pellets filled in capsules or sachets, nano-particles filled in capsules or sachets or powder filled in capsules or sachets. Preferably, the drug is present in the form of nano-particles, pellets or micro-tablets, which may optionally be filled in sachets or capsules.

Preferably, all solid oral dosage forms may be provided with an enteric coating. It may e.g. be applied onto the tablets, micro-tablets, pellets, etc., but may also be applied onto the capsules that contain them.

The oral pharmaceutical forms according to the invention may basically be prepared according to the classic compaction method and also by direct compaction and as solid dispersions according to the melting method or by means of the spray drying method. If desired, an enteric coating can be poured or sprayed in portions onto the tablet cores in a classic coating pan or applied by means of a fluidized-bed apparatus according to known processes. Subsequently, after drying has been completed, a film coat can be applied in the same apparatus.

Preferably, the fumaric acid derivatives for preparing the pharmaceutical preparations according to the invention are used in such an amount that this pharmaceutical preparation contains an amount of one or more fumaric acid derivative(s) per dosage unit which corresponds and/or is equivalent to an amount of 1 to 500 mg, preferably 10 to 300 mg, and mostly preferred 10 to 200 mg fumaric acid.

In the case of an parenteral administration via an injection (iv, im, sc, ip) the preparation is present in a form suitable for this. All customary liquid carriers suitable for the injection can be used.

According to a preferred embodiment the drug to be produced according to the invention can contain the following individually or in admixture: 10 to 500 mg dialkyl fumarate, in particular dimethyl fumarate and/or diethyl fumarate, 10 to 500 mg calcium alkyl fumarate, in particular calcium methyl fumarate and/or calcium ethyl fumarate, 0 to 250 mg zinc alkyl fumarate, in particular zinc methyl fumarate and/or zinc ethyl fumarate, 0 to 250 mg alkyl hydrogen fumarate, in particular methyl hydrogen fumarate and/or ethyl hydrogen fumarate and 0 to 250 mg magnesium alkyl fumarate, in particular magnesium methyl fumarate and/or magnesium ethyl fumarate, the sum of said amounts corresponding to an equivalent of 1 to 500 mg, preferably 10 to 300 mg and most preferred 10 to 200 mg fumaric acid.

Preparations according to the invention that are used with special preference contain exclusively dimethyl fumarate in an amount of 10 to 300 mg.

According to an especially preferred embodiment the pharmaceutical preparation is present in the form of micro-tablets or pellets. They have preferably a size and/or a mean diameter of ≤5000 micrometers, preferably 300 to 2500 micrometers, in particular 300 to 1000 micrometers for pellets and 1000 to 2500 micrometers for micro-tablets. Due to the administration of the fumaric acid derivatives in the form of micro-tablets, which is preferred according to the invention, gastrointestinal irritations and/or side effects which cannot be excluded in the administration of conventional single unit dose tablets can be further reduced. Presumably, this is based on the fact that the micro-tablets, preferably enteric coated micro-tablets, already are already distributed in the stomach and thus get into the intestine boluswise, where the active substances are released in locally smaller doses with the entire dosage being the same. Due to this, the local irritation of the epithelial cells of the intestine can be avoided, the better gastrointestinal tolerance of the micro-tablets as compared with conventional tablets resulting from this.

EXAMPLES OF PREPARATION

To explain the use according to the invention, various examples for the preparation of preferred pharmaceutical preparations are given below. The examples are for illustrations purposes only, but not to restrict the invention.

Example 1

Preparation of Film Tablets with an Enteric Coating Containing 100.0 mg of Monomethyl Fumarate-Ca Salt, which Corresponds to 78 mg of Fumaric Acid Taking the necessary precautions (breathing mask, gloves, protective clothing, etc.), 10 kg of monomethyl fumarate-Ca salt are crushed, mixed intensely and homogenized by means of a sieve 800. Then an excipient mixture of the following composition is prepared: 21 kg of starch derivative (STA-RX 1500®), 2 kg of micro-crystalline cellulose (Avicel PH 101®), 0.6 kg of polyvinyl pyrrolidone (PVP, Kollidon® 25), 4 kg of Primogel®, 0.3 kg of colloidal silicic acid (Aerosil®).

The active ingredient is added to the entire powder mixture, mixed, homogenized by means of a sieve 200 and processed with a 2% aqueous solution of polyvinyl pyrrolidone (PVP, Kollidon® 25) in the usual manner into binder granules, and then mixed with the outer phase in a dry state. The latter consists of 2 kg of a so-called FST complex containing 80% of talcum, 10% of silicic acid and 10% of magnesium stearate.

Thereafter, the mixture is pressed into convex tablets with a weight of 400 mg and a diameter of 10.0 mm by the usual method. Instead of these classic compaction methods, other methods such as direct compaction or solid dispersions according to the melting method and the spray drying method may also be used for preparing tablets.

Enteric Coating:

A solution of 2.250 kg of hydroxy propyl methyl cellulose phthalate (HPMCP, Pharmacoat HP® 50) is dissolved in a solvent mixture consisting of 2.50 l of demineralized water, 13 l of acetone Ph. Helv. VII and 13 l of ethanol (94% by weight) and then 0.240 kg of castor oil (Ph. Eur. II) is added to the solution. The solution is poured or sprayed in portions onto the tablet cores in a coating pan in a conventional manner.

After a corresponding drying, the film coating is subsequently applied. Said coating consists of a solution of Eudragit® E 12.5% 4.8 kg, talcum Ph. Eur. II 0.34 kg, titanium(VI) oxide Cronus RN 56® 0.52 kg, coloured lacquer ZLT-2 blue (Siegle) 0.21 kg, and polyethylene glycol 6000 Ph. Helv. VII 0.12 kg in a solvent mixture of 8.2 kg of 2-propanol Ph. Helv. VII, 0.06 kg of glycerine triacetate (Triacetin®) and 0.2 kg of demineralized water. Homogenous distribution in the coating pan or the fluidized bed, is followed by drying and polishing in the usual manner.

Example 2

Preparation of Enteric Coated Capsules Containing 86.5 mg of Monoethyl Fumarate-Ca Salt and 110.0 mg of Dimethyl Fumarate, which Corresponds to a Total of 150 mg of Fumaric Acid Taking the necessary precautions (breathing mask, gloves, protective clothing, etc.), 8.65 kg of monoethyl fumarate-Ca salt and 11 kg of dimethyl fumarate are intensely mixed with a mixture consisting of 15 kg of starch, 6 kg of lactose Ph. Helv. VII, 2 kg of microcrystalline cellulose (Avicel®), 1 kg of polyvinyl pyrrolidone (Kollidon® 25) and 4 kg of Primogel® and homogenized by means of a sieve 800.

Together with a 2% aqueous solution of polyvinyl pyrrolidone (Kollidon® 25) the entire powder mixture is processed in the usual manner into a binder granulate and mixed with the outer phase in the dried state. Said outer phase consists of 0.35 kg of colloidal silicic acid (Aerosil®), 0.5 kg of magnesium stearate and 1.5 kg of talcum Ph. Helv. VII. The homogeneous mixture is then filled in portions of 500.0 mg into appropriate capsules which are then provided with an enteric (gastric-acid resistant) coating consisting of hydroxy propyl ethyl cellulose phthalate and castor oil as softening agent in a customary fashion.

Example 3

Preparation of Enteric Micro-Tablets in Capsules Containing 87.0 mg of Monoethyl Fumarate-Ca Salt, 120 mg of Dimethyl Fumarate, 5.0 mg of Monoethyl Fumarate-Mg Salt and 3.0 mg of Monoethyl Fumarate-Zn Salt, which Corresponds to a Total of 164 mg of Fumaric Acid ("Forte" Tablets)

Taking the necessary precautions (breathing mask, gloves, protective clothing, etc.), 8.7 kg of monoethyl fumarate-Ca salt, 12 kg of dimethyl fumarate, 0.5 kg of monoethyl fumarate-Mg salt and 0.3 kg of monoethyl fumarate-Zn salt are crushed, intensely mixed and homogenized by means of an sieve 800. An excipient mixture of the following composition is prepared: 18 kg of starch derivative (STA-RX 1500), 0.3 kg of micro-crystalline cellulose (Avicel PH 101), 0.75 kg of PVP (Kollidon 120), 4 kg of Primogel, 0.25 kg of colloidal silicic acid (Aerosil). The entire powder mixture is added to the active ingredient mixture, homogenized by means of a 200 sieve, and processed in the usual manner with a 2% aqueous solution of polyvinyl pyrrolidone (Kollidon K25) to obtain a binder granulate and mixed in a dry state with the outer phase that consists of 0.5 kg of magnesium stearate and 1.5 kg of talcum. Then the powder mixture is pressed by the conventional method into convex micro-tablets with a gross mass of 10.0 mg and a diameter of 2.0 mm.

The enteric (gastric acid-resistant) coating is applied in a fluidized-bed apparatus. In order to achieve resistance to gastric acid, portions of a solution of 2.250 kg of hydroxy propyl methyl cellulose phthalate (HPMCP, Pharmacoat HP 50) are dissolved in a mixture of the following solvents: acetone 13 l, ethanol 94% by weight denatured with 2% ketone 13.5 l and demineralized water 2.5 l. 0.240 kg of castor oil are added as softening agent to the finished solution and applied in portions onto the tablet cores in the usual manner.

Film coat: After drying is completed, a suspension of the following composition is then applied as a film coat in the same apparatus: talcum 0.340 kg, titanium(VI) oxide Cronus RN 56 0.4 kg, coloured lacquer L red lacquer 86837 0.324 kg, Eudragit E 12.5% 4.8 kg and polyethylene glycol 6000 pH 11 XI 0.12 kg in a solvent mixture of the following composition: 2-propanol 8.17 kg, demineralized water 0.2 kg and glycerine triacetate (Triacetin) 0.6 kg.

The gastric acid-resistant micro-tablets are analyzed with respect to their ingredients and are then filled into hard gelatine capsules at a corresponding net weight and sealed.

Example 4

Preparation of Enteric Micro-Tablets in Capsules Containing 120.0 mg Dimethyl Fumarate which Corresponds to 96 mg Fumaric Acid Taking the necessary precautions (breathing mask, gloves, protective clothing, etc.) 12 kg of dimethyl fumarate are crushed and homogenized by means of a 800 sieve. An excipient mixture of the following composition is prepared: 17.5 kg of starch derivative (STA-RX® 1500), 0.30 kg of micro-crystalline cellulose (Avicel® PH 101), 0.75 kg of PVP (Kollidon® 120), 4 kg of Primogel®, 0.25 kg of colloidal silicic acid (Aerosil®). The entire powder mixture is added to the active ingredient mixture, mixed, homogenized by means of a 200 sieve, processed in the usual manner with a 2% aqueous solution of polyvinyl pyrrolidone (Kollidon® K25) to obtain a binder granulate and mixed in a dry state with the outer phase which consists of 0.5 kg of Mg stearate and 1.5 kg of talcum.

Then, the powder mixture is pressed by the conventional method into convex micro-tablets with a gross mass of 10.0 mg and a diameter of 2.0 mm.

To achieve resistance to gastric acid, portions of a solution of 2.25 kg hydroxy propyl methyl cellulose phthalate (HP-MCP, Pharmacoat® HP 50) are e.g. dissolved in a mixture of the following solvents: acetone 13 l, ethanol (94% by weight denatured with 2% ketone) 13.5 l and demineralized water 1.5 l. Castor oil (0.24 kg) is added as softening agent to the finished solution and applied in portions onto the tablet cores in the usual manner.

After drying is completed, a suspension of the following composition is then applied as a film coat in the same apparatus: talcum 0.34 kg, titanium(VI) oxide Cronus RN 56 0.4 kg, coloured lacquer L red lacquer 86837 0.324 kg, Eudragit E 12.5% 4.8 kg and polyethylene glycol 6000 pH 11 XI 0.12 kg in a solvent mixture of the following composition: 2-propanol 8.17 kg, demineralized water 0.2 kg and glycerine triacetate (Triacetin) 0.6 kg.

The gastric acid-resistant micro-tablets are analyzed with respect to their ingredients and are then filled into hard gelatine capsules at a corresponding net weight and sealed.

Example 5

Preparation of Enteric Micro-Tablets in Capsules Containing 120.0 mg of Diglycine Fumaric Acid Diamide, which Corresponds to 96 mg of Fumaric Acid 12 kg of diglycine fumaric acid diamide are crushed and homogenized as indicated above. An excipient mixture of the following composition is prepared: 23.2 kg of microcrystalline cellulose (Avicel® PH 200), 3 kg of croscarmelose sodium (AC-Di-SOL-SD-711), 2.5 kg of talcum, 0.1 kg of anhydrous silicic acid (Aerosil® 200) and 1 kg Mg stearate. The entire powder mixture is added to the active ingredient mixture and homogeneously mixed. Then, the powder mixture is pressed by the direct compaction into convex micro-tablets with a gross mass of 10.0 mg and a diameter of 2.0 mm.

Subsequently, a solution of 0.94 kg Eudragit® in isopropanol is prepared which, additionally, contains 0.07 kg dibutyl phthalate. This solution is sprayed onto the tablet cores. Then, a dispersion of 17.32 kg Eudragit® L D-55 and a mixture of 2.8 kg micro-talcum, 2 kg Macrogol 6000 and 0.07 kg Dimeticon in water is prepared and sprayed onto the cores.

Subsequently, the enteric micro-tablets are analyzed with respect to their ingredients and filled into hard gelatine capsules at a corresponding net weight and sealed.

Example 6

Preparation of Enteric Micro-Tablets in Capsules Containing 60.0 mg of r-1,t-2,c-3,t-4-Tetrakis(Methoxy Carbonyl)Cyclobutane and 30.0 mg r-1,t-2,c-3,t-4,c-5,t-6-Hexa(Methoxy Carbonyl)Cyclohexane 6.0 kg of r-1,t-2,c-3,t-4-tetrakis(methoxy carbonyl)cyclobutane and 3.0 kg of r-1,t-2,c-3,t-4,c-5,t-6-hexa(methoxy carbonyl)cyclohexane are crushed, intensely mixed and homogenized by means of sieve 800. An excipient mixture of the following composition is prepared: 18 kg of starch derivative (STA-RX 1500®), 0.30 kg of micro-crystalline cellulose (Avicel PH 101), 0.75 kg of PVP (Kollidon 120), 4.00 kg of Primogel, 0.25 kg of colloidal silicic acid (Aerosil). The active ingredient is added to the entire powder mixture and homogenized by means of a sieve 200 and processed with a 2% aqueous solution of polyvinyl pyrrolidone (Kollidon K25) in the usual manner into binder granules, and then mixed with the outer phase in a dry state. The latter consists of 0.50 kg of Mg stearate and 1.50 kg of talcum. Thereafter, the powder mixture is pressed into convex micro-tablets with a gross mass of 10.0 mg and a diameter of 2.0 mm by the usual method.

The enteric (gastric acid-resistant) coating is poured onto the tablet cores in a classic coating pan. In order to achieve resistance to gastric acid, portions of a solution of 2.250 kg of hydroxy propyl methyl cellulose phthalate (HPMCP, Pharmacoat HP 50) are dissolved in a mixture of the following solvents: acetone 13.00 l, ethanol 94% by weight denatured with 2% ketone 13.50 l and demineralized water 2.50 l. 0.240 kg of castor oil is added as softening agent to the finished solution and applied in portions to the tablet cores in the usual manner.

Film coat: After drying is completed, a suspension of the following composition is applied as a film coat in the same apparatus: talcum 0.340 kg, titanium(VI) oxide Cronus RN 56 0.400 kg, coloured lacquer L red lacquer 86837 0.324 kg, Eudragit E 12.5% 4.800 kg and polyethylene glycol 6000 pH 11 XI 0.120 kg in a solvent mixture of the following composition: 2-propanol 8.170 kg, demineralized water 0.200 kg and glycerine triacetate (Triacetin) 0.600 kg.

Subsequently, the enteric micro-tablets are analyzed with respect to their active ingredients and filled into hard gelatine capsules at a corresponding net weight and sealed.

Example 7

Preparation of a Suspension for Parenteral Application Containing 60.0 Mg of r-1,t-2,c-3,t-4-Tetrakis(Methoxy Carbonyl)Cyclobutane and 30.0 Mg r-1,t-2,c-3,t-4,c-5,t-6-Hexa(Methoxy Carbonyl) Cyclohexane

| Ingredients | mg/ml |
| --- | --- |
| r-1,t-2,c-3,t-4-tetrakis(methoxy carbonyl) cyclobutane | 60.00 |
| r-1,t-2,c-3,t-4,c-5,t-6-hexa(methoxy carbonyl) cyclohexane | 30.00 |
| Methyl cellulose | 0.25 |
| Sodium citrate, dihydrate | 30.00 |
| Benzyl alcohol | 9.00 |

-continued

| Ingredients | mg/ml |
|---|---|
| Methyl p-hydroxybenzoic acid | 1.80 |
| Propyl p-hydroxybenzoic acid | 1.20 |
| Water for injection purposes | q.s.a.d. 1.00 |

The aforementioned ingredients are processed to a parenteral suspension using standard techniques.

EXAMPLES OF APPLICATION

Example A

In Vivo Data on the Treatment of Cardiac Insufficiency with DMF Using a Rat Model The effects of dimethyl fumarate were examined in the present experiment using the model of acute ischemia and reperfusion of the rat. For this purpose, healthy, male rats were divided into three groups with 17 animals each. In the tests, an ischemia was caused for 45 minutes through an occlusion of an artery with the heart being exposed and, subsequently, reperfusion was carried out for 120 minutes. Finally, a myocardial infarction was triggered by means of a reocclusion and the risk area was determined by means of dyeing with phthalocyanine blue.

The administration of the test substance was carried out iv at the beginning of the first occlusion. The control group received 0.02% DMSO (0.5 ml/kg body weight), the DMF group received 10 mg dimethyl fumarate in 0.02% DMSO (0.5 ml/kg body weight). The animals were ischemically preconditioned in the second group (2 times 5 minutes each ischemia and reperfusion).

The results are represented in FIG. 1. Evidently, both dimethyl fumarate (DMF) and the ischemic preconditioning (IPC) limited the size of the infarction to a statistically significant degree in our experiments, the risk area being similar in all 3 groups. Thus, the data proves that the used dimethyl fumarate can significantly reduce the size of the infarction and thus prevent a cardiac insufficiency.

Example B

Inhibition of the PDGF-Induced Incorporation of Thymidine

The successful treatment of asthma involves three different pathways: (1) the reduced release of inflammatory mediators in allergic responses, (2) the inhibition of T-lymphocyte invasion, and (3) the inhibition of mesenchymal cell proliferation. Glucocorticoids, which are the treatment of choice in asthma, have been shown to inhibit mesenchymal cell proliferation. This test can thus be used to screen for possible other active substances for treatment of asthma.

BSM (bronchial smooth muscle) cells were cultivated in RPMI, 0.3% albumin and 0.1% DMSO at 37° C. in the presence of 0, 1, 5, 10 and 20 ng/ml on PDGF with and without $10^{-5}$ M dimethyl fumarate.

Figure 2:
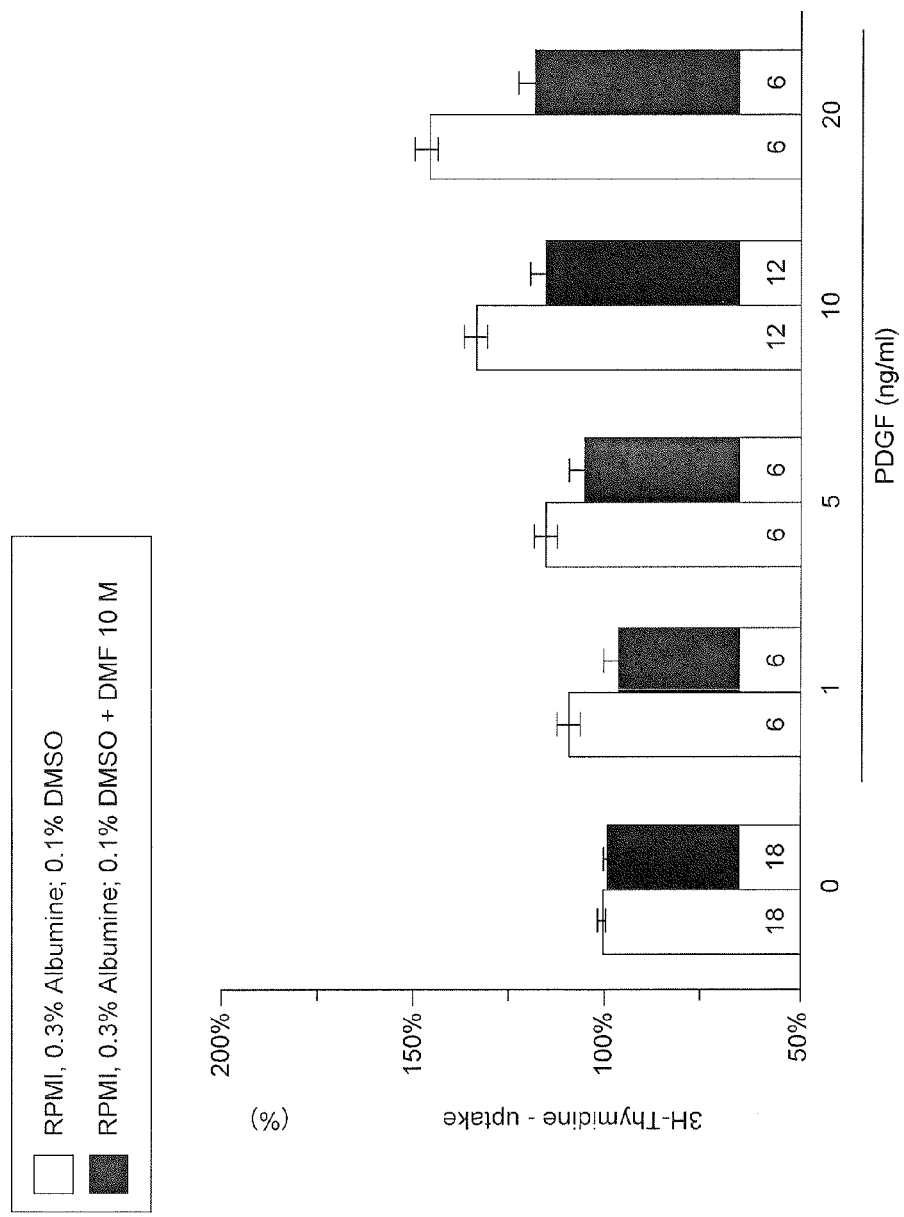
FIG. 2 shows the percentage inhibition of PDGF-induced $^3$H-thymidine incorporation in bronchial smooth muscle cells, when DMF is added.

After a predetermined period of time, 5 µCi on $^3$H-thymidine was added to the culture medium and incubation was continued for further 24 hours. The incorporation was finally stopped by means of centrifugation, removal of the supernatant, washing and lysis of the cells. The incorporation on $^3$H-thymidine was measured by determining the radioactivity in the lysates in a liquid scintillation device in comparison to the control. The results are shown in FIG. 2 as percentage values as compared with the control (100%). The addition of PDGF evidently increases the $^3$H-thymidine incorporation and, thus, cell proliferation, whereas this increase is significantly reduced upon addition of dimethyl fumarate.

Example C

Figure 3:
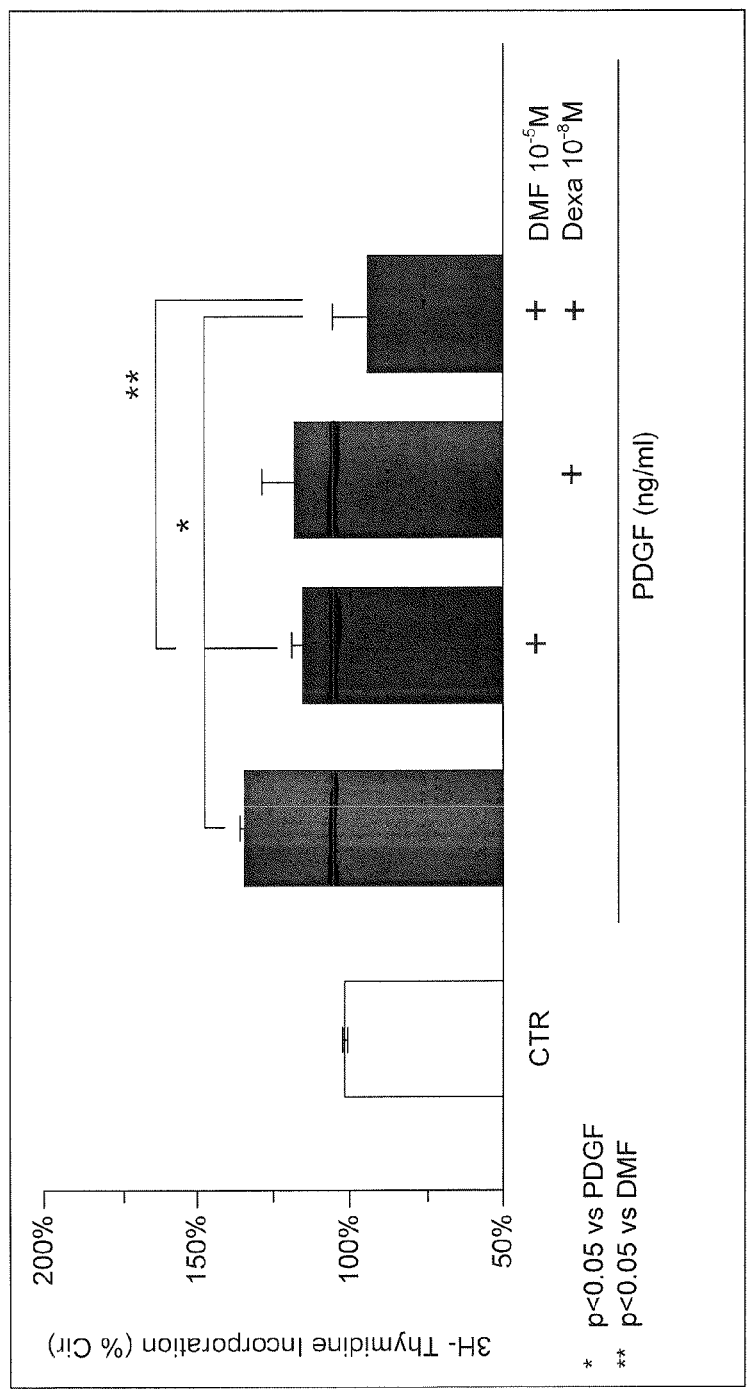
FIG. 3 is a bar chart showing percentage of cell proliferation of bronchial smooth muscle cells upon PDGF stimulation in the absence or presence of DMF and/or dexamethasone.

Bronchial smooth muscle cells were grown in 96 well plates until they reached 60-70% confluency. The cells were then starved for 48 h in serum free, 0.3% albumine containing RPMI medium. One hour before stimulation of cell proliferation with 10 ng/ml PDGF, the cells were treated with (a) $10^{-5}$ M DMF, (b) $10^{-8}$ M dexamethasone (dexa), or (c) $10^{-5}$ M DMF and $10^{-8}$ M dexa. As a control untreated cells (buffer only) were used. Cells were treated for 36 h, whereafter 4 µCi of $^3$H-thymidine was added for further 8 hours. The cells were lysed, DNA-incorporated $^3$H-thymidine bound to filter membranes, and the incorporated cpm measured in a liquid scintillation device. The results are shown in FIG. 3 in percentage of control (100%) and compared to PDGF induced proliferation.

When treating cells with dexa alone ($10^{-8}$ M), which is a therapeutically relevant dosage, cell proliferation was reduced to about 117±11%. A comparable reduction was seen with DMF at $10^{-5}$ M (116±4%). Combined administration of DMF and dexa in these concentrations resulted in a synergistic decrease of cell proliferation to nearly baseline levels (95±11%). These results show that DMF may be useful in the treatment of asthma, either as of its own, and also in combination with dexametasone or glucocorticoids in general.

In a specifically preferred embodiment for the treatment of asthma and chronically obstructive lung diseases such treatment is thus in combination with a glucocorticoid. Administration can be in the same dosage unit or in separate dosage units. Administration can also be in parallel or sequentially. Preferably the glucocorticoid is selected from the group consisting of dexamethasone, cortisone, hydrocortisone, prednisolone, prednisone, methylprednisolone, fluocortolone, triamcinolone, betamethasone, beclomethasone, budenoside, flunisonide, fluticasone, and pharmaceutically acceptable salts and derivatives thereof. Most preferably the glucocorticoid is dexamethasone.

Example D

Dahl-rats, which are salt sensitive, were administered varying dosages of DMF on a daily basis and put on a high salt diet. After 8 weeks of treatment the left ventricular enddiastolic diameters were measured for test and control groups by echocardiographic analysis. Groups measured were control (0 mg DMF; n=9); group 1 (2×5 mg DMF/kg/d; n=9) and group 2 (2×15 mg DMF/kg/d; n=11).

Figure 4:
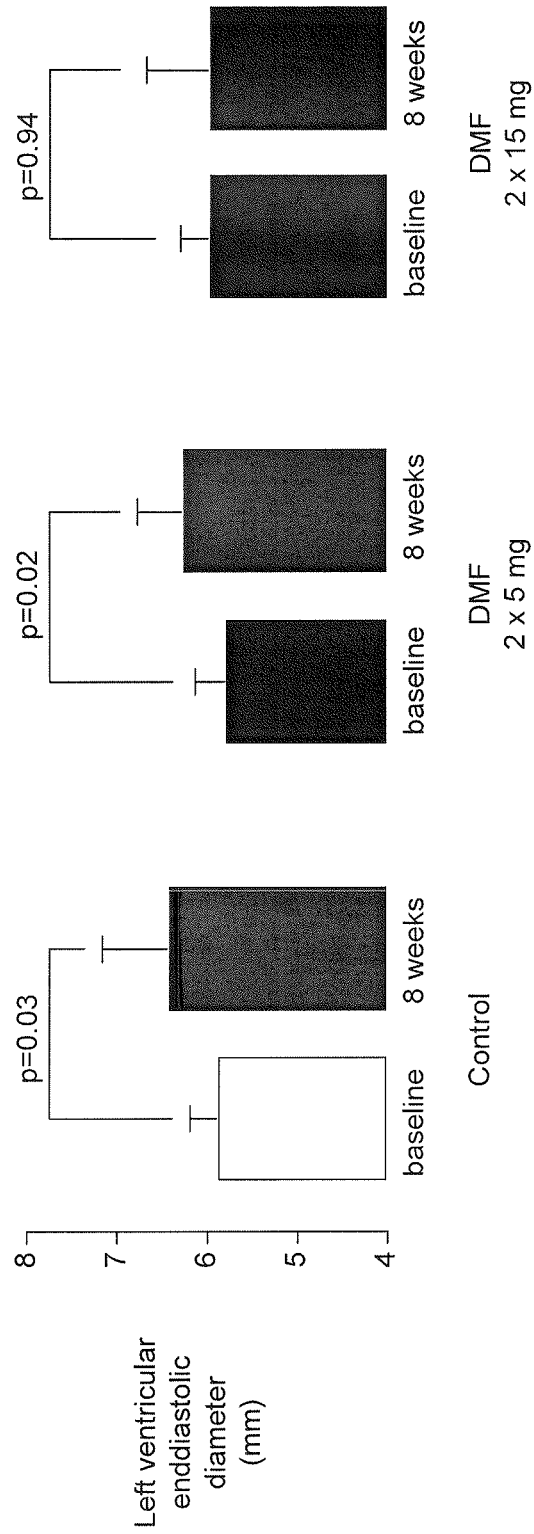
FIG. 4 is a bar chart showing left ventricular enddiastolic diameters on Dahl rats before and after 8 weeks of high salt diet in the absence and presence of DMF.

In the echocardiography analysis, DMF prevented the dilatation of the left ventricle after 8 weeks of high salt diet in dose dependent manner. Specifically, in the DMF groups the inner diameter of the left ventricle remained in the same range as at baseline (see FIG. 4). In contrast, animals in the control group showed an enlarged left ventricle indicating dilatation of the left ventricle. Importantly, dilatation of the left ventricle marks the transition from compensated hypertrophy to decompensated heart failure. Consequently, DMF delays the transition to heart failure, and thus prevents myocardial infarctions.

The invention claimed is:

1. A method for treating cardiac insufficiency, angina pectoris or a combination thereof resulting from STAT1 activation, comprising administering to a patient in need of said treating a fumaric acid derivative that is:

(a) a compound selected from the group consisting of a dialkyl fumarate, a monoalkyl hydrogen fumarate, a fumaric acid monoalkyl ester salt, a fumaric acid monoamide, a monoamido fumaric acid salt, a fumaric acid diamide, and a monoalkyl monoamido fumarate;

(b) a carbocyclic oligomer of said compound;

(c) an oxacarbocyclic oligomer of said compound; or (d) a mixture of any of the foregoing.

2. The method according to claim 1, comprising administering the fumaric acid derivative to treat left ventricular insufficiency.

3. The method according to claim 1, wherein the fumaric acid derivative is a fumaric acid dialkyl ester of the formula (I):

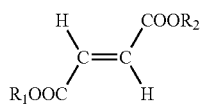

wherein $R_1$ and $R_2$ which are the same or different, independently represent a linear, branched or cyclic, saturated or unsaturated $C_{1-24}$ alkyl radical or a $C_{5-20}$ aryl radical, and wherein the $C_{1-24}$ alkyl radical or the $C_{5-20}$ aryl radical is optionally substituted with halogen, hydroxy, $C_{1-4}$ alkoxy, $C_{1-4}$ alkyl, nitro or cyano.

4. The method according to claim 1, wherein the fumaric acid derivative is a fumaric acid monoalkyl ester of the formula (II):

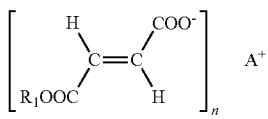

wherein $R_1$ represents a linear, branched or cyclic, saturated or unsaturated $C_{1-24}$ alkyl radical or a $C_{5-20}$ aryl radical;

A represents hydrogen, an alkaline or alkaline earth metal cation or a physiologically acceptable transition metal cation; and n equals 1 or 2 and corresponds to the valence of A.

5. The method according to claim 1, wherein the fumaric acid derivative is (i) a compound of formula (I),

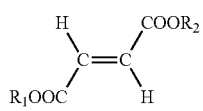

wherein $R_1$ and $R_2$ which are the same or different, independently represent a linear, branched or cyclic saturated, or unsaturated $C_{1-24}$ alkyl radical or a $C_{5-20}$ aryl radical, and wherein the $C_{1-24}$ alkyl radical or the $C_{5-20}$ aryl radical is optionally substituted with halogen, hydroxy, $C_{1-4}$ alkoxy, $C_{1-4}$ alkyl, nitro or cyano, (ii) a compound of Formula (II)

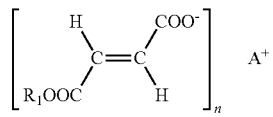

wherein $R_1$ represents a linear, branched or cyclic, saturated or unsaturated $C_{1-24}$ alkyl radical or a $C_{5-20}$ aryl radical, A represents hydrogen, an alkaline or alkaline earth metal cation or a physiologically acceptable transition metal cation, and n equals 1 or 2 and corresponds to the valence of A, or (iii) a mixture of a compound of Formula (I) and a compound of Formula (II).

6. The method according to claim 5, wherein the fumaric acid derivative is selected from the group consisting of fumaric acid dimethyl ester, fumaric acid diethyl ester, fumaric acid methyl ethyl ester, methyl hydrogen fumarate, ethyl hydrogen fumarate, calcium methyl fumarate, calcium ethyl fumarate, magnesium methyl fumarate, magnesium ethyl fumarate, zinc methyl fumarate, zinc ethyl fumarate, iron methyl fumarate, iron ethyl fumarate and mixtures thereof.

7. The method according to claim 1, wherein a pharmaceutical preparation is administered to the patient, wherein said pharmaceutical preparation comprises an amount of the fumaric acid derivative that corresponds to 1 to 500 mg of fumaric acid.

8. The method according to claim 1, wherein the fumaric acid derivative is fumaric acid dimethyl ester.

9. The method according to claim 1, wherein a pharmaceutical preparation is administered to the patient, wherein said pharmaceutical preparation comprises 10 to 500 mg of fumaric acid dimethyl ester.

10. A method for treating cardiac insufficiency, comprising administering to a patient in need of said treating a fumaric acid derivative that is:

(a) a compound selected from the group consisting of a dialkyl fumarate, a monoalkyl hydrogen fumarate, a fumaric acid monoalkyl ester salt, a fumaric acid monoamide, a monoamido fumaric acid salt, a fumaric acid diamide, and a monoalkyl monoamido fumarate;

(b) a carbocyclic oligomer of said compound;

(c) an oxacarbocyclic oligomer of said compound; or (d) a mixture of any of the foregoing.

11. The method according to claim 10, wherein the fumaric acid derivative is a fumaric acid monoalkyl ester of the formula (II):

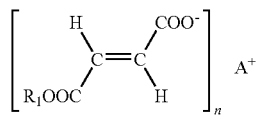

wherein $R_1$ represents a linear, branched or cyclic, saturated or unsaturated $C_{1-24}$ alkyl radical or a $C_{5-20}$ aryl radical; A represents hydrogen, an alkaline or alkaline earth metal cation or a physiologically acceptable transition metal cation; and n equals 1 or 2 and corresponds to the valence of A.

12. The method according to claim 10, wherein the fumaric acid derivative is fumaric acid dimethyl ester.

13. A method for treating angina pectoris, comprising administering fumaric acid dimethyl ester to a patient in need of said treating.

* * * * *